United States Patent
Churcher et al.

(10) Patent No.: US 6,984,663 B2
(45) Date of Patent: Jan. 10, 2006

(54) CYCLOHEXYL SULPHONES

(75) Inventors: Ian Churcher, Great Dunmow (GB); Kevin Dinnell, Much Hadham (GB); Timothy Harrison, Great Dunmow (GB); Sonia Kerrad, Sawbridgeworth (GB); Alan John Nadin, Sawbridgeworth (GB); Paul Joseph Oakley, South Benfleet (GB); Duncan Edward Shaw, Bishops Stortford (GB); Martin Richard Teall, Bishops Stortford (GB); Susannah Williams, Sawbridgeworth (GB); Brian John Williams, Great Dunmow (GB)

(73) Assignee: Merck Sharp & Dohme Limited, Hoddesdon (GB)

(*) Notice: Subject to any disclaimer, the term of this patent is extended or adjusted under 35 U.S.C. 154(b) by 20 days.

(21) Appl. No.: 10/223,993

(22) Filed: Aug. 20, 2002

(65) Prior Publication Data

US 2003/0114496 A1 Jun. 19, 2003

(30) Foreign Application Priority Data

Aug. 21, 2001 (GB) .............................................. 0120347
Aug. 21, 2001 (WO) .............................. PCT/GB01/03741

(51) Int. Cl.
  *A61K 31/19* (2006.01)
  *C07C 317/12* (2006.01)
  *C07C 317/14* (2006.01)

(52) U.S. Cl. ....................................... 514/570; 562/429
(58) Field of Classification Search ................. 562/429; 562/514/570
See application file for complete search history.

(56) References Cited

U.S. PATENT DOCUMENTS

| 2,802,013 | A | 8/1957 | Dodson |
| 2,812,330 | A | 11/1957 | Dodson |
| 5,703,129 | A | 12/1997 | Felsenstein et al. |
| 2004/0082617 | A1 | 4/2004 | Harrison et al. |
| 2004/0116404 | A1 | 6/2004 | Pineiro et al. |
| 2004/0121995 | A1 | 6/2004 | Churcher et al. |
| 2004/0122050 | A1 | 6/2004 | Churcher et al. |
| 2004/0171683 | A1 | 9/2004 | Pineiro |
| 2004/0230054 | A1 | 11/2004 | Dinnell et al. |

FOREIGN PATENT DOCUMENTS

| CA | 56026866 | 3/1981 |
| CA | 2 473 374 | 7/2003 |
| EP | 0863134 A | 9/1998 |
| JP | 5605149 | 3/1981 |
| JP | 56026847 | 3/1981 |
| WO | WO 00/50391 | 8/2000 |
| WO | WO 02/081433 | 10/2002 |
| WO | WO 02/081435 | 10/2002 |
| WO | WO 03/055850 | 7/2003 |
| WO | WO 03/059335 | 7/2003 |
| WO | WO 2004/013090 | 2/2004 |
| WO | WO 2004/031137 | 4/2004 |
| WO | WO 2004/031138 | 4/2004 |
| WO | WO 2004/031139 | 4/2004 |
| WO | WO 2004/048321 | 6/2004 |
| WO | WO 2004/101538 | 11/2004 |
| WO | WO 2004/101539 | 11/2004 |
| WO | WO 2005/000798 | 1/2005 |

OTHER PUBLICATIONS

Tetrahedron (1982), 38(8), 1051–1057.*
* This reference is not being furnished because it is not being used in a rejection against applicants claims.*
L. Capuano: et al.; Chemische Berichte, vol. 112, No. 3, Mar. 1979, pp. 1012–1022.
J.M. Decesare, et al.: Canadian Journal of Chemistry., vol. 59, No. 10, May 15, 1981, pp. 1415–1424.
O. Eisleb: Berichte Der Deutschen Chemischen Gesellschaft, vol. 74, No. 8, 1941, pp. 1433–1450.
J. Golinski, et al.: Synthesis, No. 6, Jun. 1979, pp. 461–463.
P. Kisanga, et al.: Journal of the American Chemical Society, vol. 122, No. 41, Oct. 18, 2000, pp. 10017–10026.
C. Koradin, et al.: SYNLETT, No. 10, Oct. 2000, paes 1452–1454.
T. Oyuyama, et al.: Bulletin of the Chemical Society of Japan, vol. 64, No. 9, Sep. 1991, pp. 2751–2756.
M. Makosza et al., "Ambiphilic Reactivity of 2,4–Dinitrobenzyl p–Tolyl Sulfone Carbanion", Polish J. Chem., vol. 72, pp. 1198–1201 (1998).
J. P. Scott et al., "Expedient Diels–Alder assembly of 4–aryl–4–phenylsulfonyl cyclohexanones", Tetrahedron Letters, vol. 45, pp. 3345–3348 (2004).
E. W. Garbisch et al., "On the Mechanism of Benzylic Substituent Hydrogenolysis", Journl of the American Chemical Society, vol. 89(16), pp. 4233–4235 (1967).
R. K. Norris et al., "An Example of Substitution proceeding with Retention in the SRN1 Reaction. Trapping of a Pyramidal Benzylic Radical by Benzenethiolate Ion", J. of the Chem. Soc. Chem. Comm., Issue 3, pp. 79–80 (1981).
U.S. Patent Application Ser. No. 10/957,251, filed Oct. 1, 2004.

* cited by examiner

Primary Examiner—Taofiq Solola
Assistant Examiner—Rebecca Anderson
(74) Attorney, Agent, or Firm—John C. Todaro; Melvin Winokur

(57) ABSTRACT

Novel sulphones of formula I are disclosed:

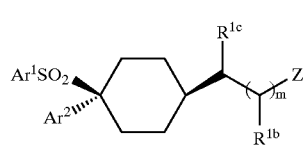

The compounds modulate the processing of amyloid precursor protein by gamma-secretase, and hence are useful in the treatment or prevention of Alzheimer's disease.

11 Claims, No Drawings

CYCLOHEXYL SULPHONES

CROSS REFERENCE TO RELATED APPLICATIONS

This application claims priority under 35 U.S.C. § 119 from GB Application No. 0120347.0, filed Aug. 21, 2001 and from WO Application No. PCT/GB01/03741, filed Aug. 21, 2001.

The present invention relates to a novel class of compounds, their salts, pharmaceutical compositions comprising them, processes for making them and their use in therapy of the human body. In particular, the invention relates to novel sulphones which modulate the processing of APP by y-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2):1–7; ID *research alert* 1997 2(1):1–8; Current Opinion in CPNS Investigational Drugs 1999 1(3):327–332; and Chemistry in Britain, Jan. 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

The present invention provides a novel class of non-peptidic compounds which are useful in the treatment or prevention of AD by modulating the processing of APP by the putative γ-secretase, thus arresting the production of Aβ.

The present invention provides a compound of formula I:

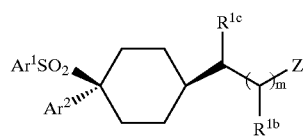

wherein:

m is 0 or 1;

Z represents halogen, CN, $NO_2$, $N_3$, $CF_3$, $OR^{2a}$, $N(R^{2a})_2$, $CO_2R^{2a}$, $OCOR^{2a}$, $COR^{2a}$, $CON(R^{2a})_2$, $OCON(R^{2a})_2$, $CONR^{2a}(OR^{2a})$, $CON(R^{2a})N(R^{2a})_2$, $CONHC(=NOH)R^{2a}$, heterocyclyl, phenyl or heteroaryl, said heterocyclyl, phenyl or heteroaryl bearing 0–3 substituents selected from halogen, CN, $NO_2$, $CF_3$, $OR^{2a}$, $N(R^{2a})_2$, $CO_2R^{2a}$, $COR^{2a}$, $CON(R^{2a})_2$ and $C_{1-4}$alkyl;

$R^{1b}$ represents H, $C_{1-4}$alkyl or OH;

$R^{1c}$ represents H or $C_{1-4}$alkyl;

with the proviso that when m is 1, $R^{1b}$ and $R^{1c}$ do not both represent $C_{1-4}$alkyl;

$Ar^1$ represents $C_{6-10}$aryl or heteroaryl, either of which bears 0–3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents $C_{6-10}$aryl or heteroaryl, either of which bears 0–3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy;

$R^{2a}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, $OR^{2b}$, $CO_2R^{2b}$, $N(R^{2b})_2$, $CON(R^{2b})_2$, Ar and COAr; or $R^{2a}$ represents Ar; or two $R^{2a}$ groups together with a nitrogen atom to which they are mutually attached may complete an N-heterocyclyl group bearing 0–4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

$R^{2b}$ represents H, $C_{1-6}$alkyl, $C_{3-6}$cycloalkyl, $C_{3-6}$cycloalkyl$C_{1-6}$alkyl, $C_{2-6}$alkenyl, any of which optionally bears a substituent selected from halogen, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr; or $R^{2b}$ represents Ar; or two $R^{2b}$ groups together with a nitrogen atom to which they are mutually attached may complete an N-heterocyclyl group bearing 0–4 substituents independently selected from =O, =S, halogen, $C_{1-4}$alkyl, CN, $NO_2$, $CF_3$, OH, $C_{1-4}$alkoxy, $C_{1-4}$alkoxycarbonyl, $CO_2H$, amino, $C_{1-4}$alkylamino, di($C_{1-4}$alkyl)amino, carbamoyl, Ar and COAr;

Ar represents phenyl or heteroaryl bearing 0–3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom of said aromatic ring is other than C;

or a pharmaceutically acceptable salt thereof.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl, "$C_{2-6}$alkynyl" and "$C_{1-6}$alkoxy" are to be construed in an analogous manner.

The expression "$C_{3-6}$cycloalkyl" as used herein refers to nonaromatic monocyclic or fused bicyclic hydrocarbon ring systems comprising from 3 to 6 ring atoms. Examples include cyclopropyl, cyclobutyl, cyclopentyl, cyclohexyl, and cyclohexenyl.

The expression "$C_{3-6}$cycloalkyl$C_{1-6}$alkyl" as used herein includes cyclopropylmethyl, cyclobutylmethyl, cyclopentylmethyl and cyclohexylmethyl.

The expression "$C_{6-10}$aryl" as used herein includes phenyl and naphthyl. Phenyl is preferred.

The expression "heterocyclyl" as used herein means a cyclic or polycyclic system of up to 10 ring atoms selected from C, N, O and S, wherein none of the constituent rings is aromatic and wherein at least one ring atom is other than carbon. Preferred heterocyclyl groups contain 3–7 ring atoms, most preferably 4–6 ring atoms. Examples of heterocyclyl groups include azetidinyl, pyrrolidinyl, tetrahydrofuryl, piperidinyl, piperazinyl, morpholinyl, thiomorpholinyl, imidazolidinyl, oxazolidinyl, thiazolidinyl, 2,5-diazabicyclo[2.2.1]heptyl, 2-aza-5-oxabicyclo[2.2.1] heptyl and 1,4-dioxa-8-azaspiro[4.5]decanyl. Unless otherwise indicated, heterocyclyl groups may be bonded through a ring carbon atom or a ring nitrogen atom where present. "C-heterocyclyl" indicates bonding through carbon, while "N-heterocyclyl" indicates bonding through nitrogen.

The expression "heteroaryl" as used herein means a cyclic or polycyclic system of up to 10 ring atoms selected from C, N, O and S, wherein at least one of the constituent rings is aromatic and comprises at least one ring atom which is other than carbon. Where a heteroaryl ring comprises two or more atoms which are not carbon, not more than one of said atoms may be other than nitrogen. Preferred heteroaryl groups contain 5 or 6 ring atoms in total. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, benzenesulphonic acid, methanesulphonic acid, fumaric acid, maleic acid, succinic acid, acetic acid, benzoic acid, oxalic acid, citric acid, tartaric acid, carbonic acid or phosphoric acid. Alternatively, where the compounds of the invention carry an acidic moiety, pharmaceutically acceptable salts may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic ligands, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, certain compounds in accordance with the invention may exist as enantiomers by virtue of the asymmetry of the molecule as a whole. It is to be understood that in such cases both enantiomers, and mixtures thereof in any proportion, are included within the scope of the invention, and that structural formulae depicting molecules of this type shall be representative of both of the possible enantiomers, unless otherwise indicated.

In the compounds of formula I, $Ar^1$ typically represents optionally substituted phenyl or heteroaryl. Typical heteroaryl embodiments of $Ar^1$ include optionally substituted pyridyl, in particular optionally substituted 3-pyridyl. $Ar^1$ is preferably selected from phenyl groups substituted in the 4-position with halogen, methyl or trifluoromethyl, and phenyl groups substituted in the 3- and 4-positions by halogen. In a preferred embodiment of the invention $Ar^1$ represents 4-chlorophenyl. In another preferred embodiment $Ar^1$ represents 4-trifluoromethylphenyl.

$Ar^2$ is typically selected from phenyl groups substituted in the 2- and 5-positions by halogen. In a preferred embodiment of the invention, $Ar^2$ represents 2,5-difluorophenyl.

In a particular embodiment, $Ar^1$ is 4-chlorophenyl or 4-trifluoromethylphenyl and $Ar^2$ is 2,5-difluorophenyl.

$R^{1b}$ typically represents H, methyl or OH, preferably H.

$R^{1c}$ typically represents H or methyl, preferably H.

Z is typically selected from CN, $N_3$, $OR^{2a}$, $N(R^{2a})_2$, $CO_2R^{2a}$, $COR^{2a}$, $CON(R^{2a})_2$, $OCON(R^{2a})_2$, $CONR^{2a}(OR^{2a})$, $CON(R^{2a})N(R^{2a})_2$, and optionally substituted phenyl or heteroaryl.

In one embodiment of the invention m is 0. In an alternative embodiment of the invention m is 1. Aptly, m is 1.

When m is 1 and $R^{1b}$ is OH, Z preferably represents optionally substituted phenyl or heteroaryl.

Particular values of $R^{2a}$ include H, aryl (such as phenyl), heteroaryl (such as pyridyl), $C_{3-6}$cycloalkyl (such as cyclopropyl, cyclobutyl and cyclopentyl), $C_{3-6}$cycloalkyl$C_{1-6}$ alkyl (such as cyclopropylmethyl), $C_{2-6}$alkenyl (such as allyl), and linear or branched $C_{1-6}$alkyl which is optionally substituted with $CF_3$, Ar, $OR^{2b}$, $N(R^{2b})_2$, $CO_2R^{2b}$ or $CON(R^{2b})_2$.

Examples of N-heterocyclyl groups represented by $N(R^{2a})_2$ include piperidin-1-yl (optionally substituted with OH, $CO_2H$, $CO_2C_{1-4}$alkyl, Me or Ph), piperazin-1-yl (optionally substituted with Me or Ph), morpholin-4-yl, thiomorpholin-4-yl, 1,1-dioxo-thiomorpholin-4-yl, 2-oxo-imidazolidin-1-yl, 5,5-dimethyl-2,2-dioxo-oxazolidin-3-yl, 2,5-dioxo-imidazolidin-1-yl, 2-oxo-oxazolidin-3-yl, 2-oxo-pyridin-1-yl, and 2-oxo-pyrrolidin-1-yl.

$R^{2b}$ typically represents H or $C_{1-4}$alkyl.

When Z represents $OR^{2a}$, $R^{2a}$ aptly represents H, Ar (especially heteroaryl such as pyridyl), alkyl (such as methyl, ethyl, propyl or butyl), or substituted alkyl (especially $CH_2Ar$ such as benzyl or pyridylmethyl).

When Z represents $N(R^{2a})_2$, the $R^{2a}$ groups aptly complete an N-heterocyclyl group which is optionally substituted as described above. Preferred substituents include =O and methyl. Specific examples of N-heterocyclyl groups represented by Z include succinimidyl, morpholin-4-yl, 2-oxo-imidazolidin-1-yl, 5,5-dimethyl-2,2-dioxo-oxazolidin-3-yl, 2,5-dioxo-imidazolidin-1-yl, 2-oxo-oxazolidin-3-yl, 2-oxo-pyridin-1-yl, and 2-oxo-pyrrolidin-1-yl.

When Z represents $CO_2R^{2a}$, $R^{2a}$ aptly represents H or alkyl (such as methyl, ethyl, propyl or butyl). In a preferred embodiment of the invention, Z represents $CO_2H$ or a pharmaceutically acceptable salt thereof.

When Z represents $COR^{2a}$, $R^{2a}$ aptly represents Ar, especially heteroaryl, and in particular 5-membered heteroaryl such as 1,2,4-triazol-3-yl.

When Z represents $CON(R^{2a})_2$ or $OCON(R^{2a})_2$, the $R^{2a}$ groups independently represent H or optionally substituted alkyl, cycloalkyl, cycloalkylalkyl or alkenyl, or together complete an N-heterocyclyl group. Very aptly, one $R^{2a}$ represents H and the other represents alkyl (such as methyl, ethyl, n-propyl, isopropyl, n-butyl, sec-butyl, tert-butyl or 1-ethylpropyl), alkenyl (such as allyl), cycloalkyl (such as cyclopropyl, cyclobutyl or cyclopentyl), cycloalkylalkyl (such as cyclopropylmethyl) or substituted alkyl (such as alkyl substituted with Ar, especially 2-pyridylethyl, 3-(imidazol-1-yl)propyl or 2-phenylethyl; or alkyl substituted with $CF_3$, $CO_2R^{2b}$, or $CON(R^{2b})_2$, especially 2,2,2-trifluoroethyl, methoxycarbonylmethyl or carbamoylmethyl). Alternatively, the two $R^{2a}$ groups complete an N-heterocyclyl group, such as morpholine, thiomorpholine, thiomorpholine-1,1-dioxide, 4-methylpiperazine, 4-phenylpiperazine, piperidine, 4-hydroxypiperidine or piperidine which is substituted in the 3- or 4-position with $CO_2R^{2b}$ and/or $C_{1-4}$alkyl, especially 3- or 4-carboxypiperidine, 3- or 4-ethoxycarbonylpiperidine, 3-carboxy-3-methylpiperidine and 3-ethoxycarbonyl-3-methylpiperidine.

When Z represents $CONR^{2a}(OR^{2a})$, each $R^{2a}$ aptly represents H or alkyl, such as methyl.

When Z represents $CON(R^{2a})N(R^{2a})_2$, each $R^{2a}$ aptly represents H or alkyl. Specific examples include $CONHNH_2$ and $CONHNH^tBu$.

When Z represents $CONHC(=NOH)R^{2a}$, $R^{2a}$ aptly represents alkyl such as methyl or ethyl.

Heteroaryl groups represented by Z are very aptly 5-membered, such as tetrazole, triazole, thiazole, thiadiazole, oxadiazole, pyrazole and imidazole, which are typically unsubstituted or substituted with methyl or hydroxy groups. The keto-tautomers of hydroxy-substituted heteroaryl groups are to be considered interchangeable with the enol forms. Specific examples include 1,2,3,4-tetrazol-1-yl, 1,2,3,4-tetrazol-2-yl, 1,2,3,4-tetrazol-5-yl, 3-hydroxy-1,2,4-triazol-5-yl, 1,2,4-triazol-3-yl, 5-methyl-1,2,4-triazol-3-yl, 2,5-dimethyl-1,2,4-triazol-3-yl, 1,3,4-oxadiazol-2-yl, 5-methyl-1,3,4-oxadiazol-2-yl, 5-methyl-1,3,4-thiadiazol-2-yl, 3-methyl-1,2,4-oxadiazol-5-yl, imidazol-2-yl, imidazol-1-yl, 4-methylthiazol-2-yl, pyrazol-1-yl, 1,2,3-triazol-1-yl, 1,2,4-triazol-1-yl, and 1,2,3-triazol-2-yl.

Examples of individual compounds in accordance with formula I are provided in the Examples section appended hereto.

The compounds of formula I have an activity as modulators of the processing of APP by γ secretase.

The invention also provides pharmaceutical compositions comprising one or more compounds of formula I or the pharmaceutically acceptable salts thereof and a pharmaceutically acceptable carrier. For use in said compositions, compounds of formula I which comprise a carboxylic acid group are preferably in the form of the free acid or the sodium salt thereof. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 250 mg, for example 1, 2, 5, 10, 25, 50, 100, 200 or 250 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly (vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

The present invention further provides a method of treatment of a subject suffering from or prone to a condition associated with the deposition of β-amyloid which comprises administering to that subject an effective amount of a compound according to formula I or a pharmaceutically acceptable salt thereof. Preferably the condition is a neurological disease having associated β-amyloid deposition such as Alzheimer's disease.

For treating or preventing Alzheimer's Disease, a suitable dosage level is about 0.01 to 250 mg/Kg per day, preferably about 0.10 to 100 mg/Kg per day, especially about 1.0 to 50 mg/Kg, and for example about 10 to 30 mg/Kg of body weight per day. Thus, a dose of about 500 mg per person per day may be considered. The compounds may be administered on a regimen of 1 to 4 times per day. In some cases, however, dosage outside these limits may be used.

Compounds of formula I in which m is 0 and Z is $CO_2R^{2a}$, $CON(R^{2a})_2$, $CONR^{2a}(OR^{2a})$, $CON(R^{2a})N(R^{2a})_2$ or $CONHC(=NOH)R^{2a}$ may be prepared by coupling of a carboxylic acid (1) with (respectively) $R^{2a}OH$, $HN(R^{2a})_2$, $HNR^{2a}(OR^{2a})$, $HN(R^{2a})N(R^{2a})_2$ or $H_2NC(=NOH)R^{2a}$,

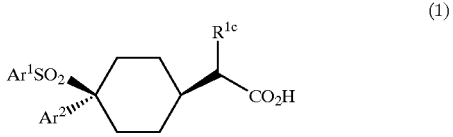

(1)

where $Ar^1$, $Ar^2$, $R^{1c}$ and $R^{2a}$ have the same meanings as before. Any of the standard coupling techniques may be used, including the use of coupling agents such as dimethylaminopyridine, hydroxybenzotriazole, dicyclohexylcarbodiimide, carbonyldiimidazole and the like. In one preferred method, the acid is converted to the corresponding acid chloride (e.g. by treatment with oxalyl chloride in DMF solution) and reacted directly with the desired nucleophile. In another preferred method, the acid is converted to an active ester derivative such as the pentafluorophenol ester (e.g. by coupling with the phenol in the presence of dicyclohexyl carbodiimide), and this intermediate is reacted with the desired nucleophile.

The acids (1) are available by hydrolysis of the esters (2), typically under alkaline conditions such as treatment with LiOH in ethanol solution:

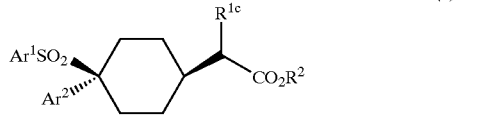

(2)

where $R^2$ represents alkyl such as methyl or ethyl, and $Ar^1$, $Ar^2$ and $R^{1c}$ have the same meanings as before.

The esters (2) are available by reduction of the alkylidene derivatives (3), optionally followed by alkylation with ($C_{1-4}$alkyl)-L where L is a leaving group (especially bromide or iodide) when $R^{1c}$ is other than H:

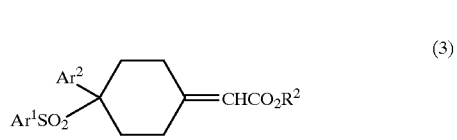

(3)

where $Ar^1$, $Ar^2$ and $R^2$ have the same meanings as before. The reduction may be carried out using sodium borohydride and nickel(II) chloride in ethanol, while the optional alkylation may be effected by treating the ester (2, $R^{1c}$=H)) with strong base (e.g. sodium bis(trimethylsilyl)amide) in an aprotic solvent at low temperature, followed by treatment with ($C_{1-4}$alkyl)-L and warming to room temperature.

If desired, the unsaturated esters (3) may be hydrolysed to the corresponding acids and converted to amides by reaction with $HN(R^{2a})_2$ prior to reduction of the olefinic bond.

The unsaturated esters (3) are available from condensation of a ketone (4) with $Ph_3P=CHCO_2R^2$:

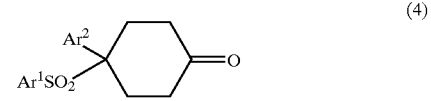

(4)

where $Ar^1$, $Ar^2$ and $R^2$ have the same meanings as before, while the ketones (4) are available by decarboxylation of the enols (5), which in turn are formed by reaction of a sulphone (6) with at least two equivalents of an acrylate (7):

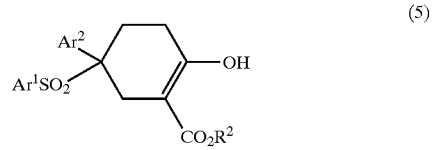

(5)

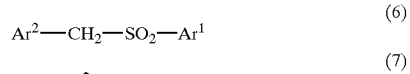

(6)

(7)

where $Ar^1$, $Ar^2$ and $R^2$ have the same meanings as before. The decarboxylation may be accomplished by heating at 150° C. in DMSO in the presence of sodium chloride and water, while reaction of (6) with (7) may be carried out at ambient temperature in an inert solvent such as THF in the presence of strong base such as potassium t-butoxide.

Alternatively, the ketones (4) may be prepared by reaction of vinyl sulphones (6a) with 2-trimethylsilyloxybutadiene:

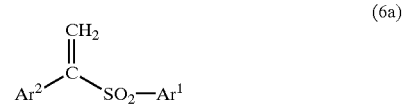

(6a)

where $Ar^1$ and $Ar^2$ have the same meanings as before. The reaction may be carried out by heating the reactants at 130° C. in xylene, then hydrolysing the resulting silyl enol ether with aqueous acid. The vinyl sulphones (6a) may be prepared by reaction of benzyl sulphones (6) with N,N,N',N'-tetramethyldiaminomethane and acetic anhydride in DMF at 60° C.

The sulphones (6) are prepared by oxidation of thioethers $Ar^2$—$CH_2$—$SAr^1$ (8), which in turn are formed by reaction of thiols $Ar^1SH$ (9) with benzyl derivatives $Ar^2CH_2$-L (10), where L is a leaving group such as chloride or bromide and Ar$^1$ and Ar$^2$ have the same meanings as before. The reaction between (9) and (10) takes place in an inert solvent such as dichloromethane in the presence of a base such as triethylamine, or alternatively in aqueous alcoholic solution in the presence of alkali such as sodium hydroxide. The oxidation of (8) to (6) is conveniently effected by m-chloroperoxybenzoic acid in an inert solvent such as dichloromethane, or alternatively by hydrogen peroxide in a water-toluene mixture in the presence of sodium tungstate and a phase transfer catalyst.

Compounds of formula I in which m is 0 and Z is COR$^{2c}$ may be prepared by treatment of the corresponding compounds in which Z is CONR$^{2c}$(OR$^{2c}$) with R$^{2c}$—Li, where R$^{2c}$ represents R$^{2a}$ which is other than H. The reaction is typically carried out in an aprotic solvent at low temperature, and is particularly useful when R$^{2c}$ in COR$^{2c}$ represents aryl or heteroaryl. In such cases, subsequent reduction of the carbonyl group (e.g. using sodium borohydride) provides the compounds of formula I in which m is 1, R$^{1b}$ is OH and Z is aryl or heteroaryl.

Compounds of formula I in which m is 0 and Z is halogen, CN, N$_3$, OR$^{2a}$, N(R$^{2a}$)$_2$ or heteroaryl bonded through N may be obtained by reaction of a sulphonate ester (11) with (respectively) halide ion, cyanide ion, azide ion, R$^{2a}$OH, HN(R$^{2a}$)$_2$ or heteroaryl comprising NH in the ring:

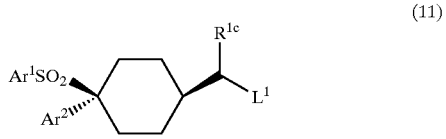

(11)

where L$^1$ represents a sulphonate leaving group (such as mesylate, tosylate or triflate) and Ar$^1$, Ar$^2$ and R$^{2a}$ have the same meanings as before. The displacement reaction may be carried out in DMF at elevated temperature, e.g. about 80° C. When the nucleophile is R$^{2a}$OH, HN(R$^{2a}$)$_2$ or heteroaryl comprising NH in the ring, it is advantageous to generate the corresponding anion by treatment with sodium hydride prior to reaction with (11).

The sulphonates (11) are prepared by reaction of the alcohols (12) with the appropriate sulphonyl chloride (e.g. under anhydrous conditions at low temperature in the presence of a tertiary amine).

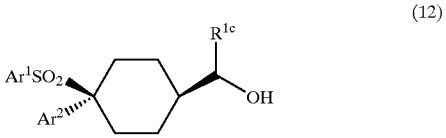

(12)

The alcohols (12) are available from the hydroboration of alkenes (13):

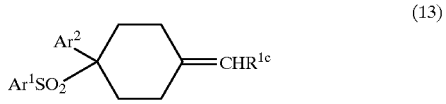

(13)

wherein Ar$^1$, Ar$^2$ and R$^{1c}$ have the same meanings as before. The process typically involves reaction with borane in THF at room temperature, followed by treatment with alkaline hydrogen peroxide and separation of the desired cis isomer by chromatography. Alkenes (13) are available from ketones (4) by condensation with Ph$_3$P=CHR$^{1c}$ where R$^{1c}$ has the same meaning as before.

An alternative route to the alcohols (12) in which R$^{1c}$ is H involves reduction of a ketone (4) (e.g. using borohydride) to the corresponding secondary alcohol (14), converting said alcohol (14) to the corresponding mesylate (or equivalent leaving group), effecting nucleophilic displacement with cyanide ion, hydrolysing the resulting nitrile to the corresponding carboxylic acid, followed by reduction to the primary alcohol. The hydrolysis is typically carried out under acid conditions (e.g. in a mixture of acetic acid and conc. HCl at 110° C.) and the reduction is conveniently carried out by sequential treatment with isobutyl chloroformate and borohydride in THF.

Compounds of formula I in which m is 0 and Z is OCOR$^{2a}$ or OCON(R$^{2a}$)$_2$ are available by reaction of alcohols (12) with (respectively) R$^{2a}$COCl or R$^{2a}$—NCO in accordance with standard procedures.

Compounds of formula I in which m is 0 and Z represents aryl or heteroaryl bonded through C may be prepared by reaction of a sulphonyl derivative (11) with the appropriate aryllithium or heteroaryllithium. Alternatively, the corresponding compounds in which Z represents a functional group such as CN, CO$_2$H, CONH$_2$, CONHNH$_2$ or CONHC (=NOH)R$^{2a}$ may be converted to heteroaryl derivatives using conventional techniques of heterocyclic synthesis. Examples of such conversions include:

treatment of a nitrile derivative with azide to form a tetrazol-5-yl derivative;

treatment of a nitrile derivative with methanol and HCl, followed by a hydrazide, to form a 5-substituted-1,3,4-oxadiazol-3-yl derivative;

treatment of a hydrazide derivative with triethylorthoformate to form a 1,3,4-oxadiazol-3-yl derivative;

treatment of a hydrazide derivative with acetamidine to form a 5-methyl-1,2,4-triazol-3-yl derivative;

treatment of an amide derivative with Lawesson's reagent, followed by a chloromethyl ketone, to form a 4-substituted-thiazol-2-yl derivative;

treatment of a carboxylic acid derivative (or active ester thereof) with semicarbazide to form a 1,2,4-triazol-3-one derivative;

treatment of a carboxylic acid derivative (or active ester thereof) with a hydrazide, followed by Lawesson's reagent, to form a 5-substituted-1,3,4-thiadiazol-2-yl derivative; and treatment of a CONHC(=NOH)R$^{2a}$ derivative with strong base (e.g. potassium t-butoxide) to form a 3-substituted-1,2,4-oxadiazol-5-yl derivative.

Illustrations of these conversions are provided in the Examples appended hereto.

Compounds of formula I in which m is 1 and R$^{1b}$ is H or C$_{1-4}$alkyl may be obtained via oxidation of an alcohol (12) to the corresponding aldehyde or ketone, and elaboration of the carbonyl group thereof in the manner described previously in connection with conversion of the ketones (4) into compounds of formula I in which m is 0.

Preferred routes to the compounds of formula I in which m is 1 and R$^{1b}$ and R$^{1c}$ are both H involve the nitrites (14):

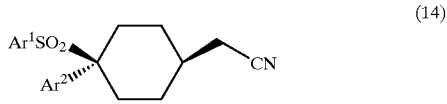

(14)

where Ar$^1$ and Ar$^2$ have the same meanings as before. The nitrites (14) are available by reaction of the sulphonates (11) in which R$^{1c}$ is H with cyanide ion as described previously, or (more preferably) by condensation of ketones (4) with diethyl (cyanomethyl)phosphonate and reduction of the resulting cyclohexylidene-acetonitriles with L-Selectride™. The condensation is typically carried out in THF at about −5° C. in the presence of potassium t-butoxide, and the reduction is typically carried out in THF at −60° C.

Reduction of nitriles (14) with diisobutylaluminium hydride (DIBAL) in toluene at −60° C., followed by acid hydrolysis, provides the aldehydes (15), which may be further reduced to the alcohols (16) using sodium borohydride in a ethanol/toluene mixture at 4° C.:

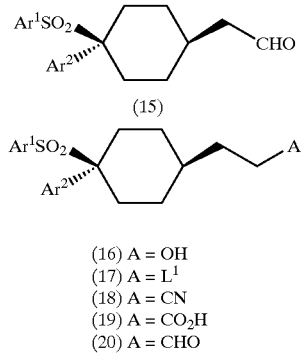

(15)

(16) A = OH
(17) A = L$^1$
(18) A = CN
(19) A = CO$_2$H
(20) A = CHO where Ar$^1$ and Ar$^2$ have the same meanings as before. The alcohols (16) may be converted to the sulphonate esters (17) (where L$^1$ has the same meaning as before) and thence to the nitrites (18) by the methods disclosed above in connection with compounds (11) and (12). The nitriles (18) may be converted to the acids (19) by acid hydrolysis or, more preferably, by treatment with DIBAL in toluene at −60° C. followed by quenching in aqueous acid to form the homologated aldehydes (20), then oxidation to the acids (19), e.g. using an aqueous mixture of sodium chlorite and sulphamic acid.

Alternatively, the homologated aldehydes (20) may be obtained from the aldehydes (15) by a Wittig-type reaction with (methoxymethyl)triphenylphosphonium chloride, then hydrolysis of the resulting enol ethers with aqueous acid. The Wittig reaction may be carried out in toluene in the presence of potassium t-butoxide, while the hydrolysis takes place in a mixture of DMF and aqueous hydrochloric acid at ambient temperature.

The cyclohexanepropanoic acids (19) may be converted into other compounds of formula I by routes similar to those described above in connection with the cyclohexaneacetic acids (1).

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. In particular, certain products may be formed as mixtures of cis and trans isomers in which a particular ring substituent is on the same or opposite side of the ring as the arylsulphonyl group. Such mixtures may be separated by conventional means such as fractional crystallisation and preparative chromatography.

Certain compounds according to the invention may exist as optical isomers due to the presence of one or more chiral centres or because of the overall asymmetery of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50–70% confluency. 10 mM sodium butyrate is added 4 hours prior to plating.
2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH 7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% CO$_2$.
5) Prepare reagents necessary to determine amyloid peptide levels, for example by Homogeneous Time Resolved Fluorescence (HTRF) assay.
6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4–0.8. (Mix briefly before reading to disperse the reduced formazan product).
11) Quantitate amyloid beta 40 peptide using an HTRF plate reader.

Alternative assays are described in *Biochemistry*, 2000, 39(30), 8698–8704.

See also, *J. Neuroscience Methods*, 2000, 102, 61–68.

The Examples of the present invention all had an ED$_{50}$ of less than 1 μM, typically less than 0.1 μM and in many cases less than 10 nM in at least one of the above assays.

The following examples illustrate the present invention.

EXAMPLES

Intermediate 1

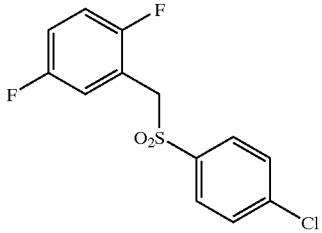

Method (a)

4-Chlorothiophenol (3.6 g, 0.025 mol) in dichloromethane (100 ml) was treated with 2,5-difluorobenzyl bromide (5.17 g, 0.025 mol) and triethylamine (3.9ml, 0.028 mol), reaction was stirred for 2 hours then diluted with dichloromethane (250 ml) and washed with water (100 ml) and brine (100 ml). The separated organic layer was dried (MgSO$_4$) and evaporated to dryness. Product was purified by passing down a plug of silica eluting with hexane-ethyl acetate mixtures. 5.12 g. $^1$H NMR CDCl$_3$ 7.23 (4H,s), 6.69–6.86 (3H,m) and 4.04 (2H,s).

This thioether (5.12 g, 0.018 mol) was dissolved in dichloromethane (100 ml) and treated with m-chloroperoxybenzoic acid (14.3 g, 0.042 mol (50% w/w)) and stirred for 2 hours. The reaction was then washed with Na$_2$S$_2$O$_5$ (5% solution, 100 ml), brine (50 ml), dried (MgSO$_4$) and evaporated to dryness. The sulphone product was purified on silica eluting with hexane-ethyl acetate mixtures, 3.6 g. $^1$H NMR CDCl$_3$ 7.61 (2H,d, J=8.6 Hz), 7.45 (2H,d, J=8.6 Hz), 7.13–7.08 (1H,m), 7.05–7.00 (1H,m), 6.99–6.87 (1H,m) and 4.36 (2H,s).

Method (b)

4-Chlorothiophenol (253 g, 1.75 mol) was dissolved in industrial methylated spirits (1265 mL) and 2M sodium hydroxide solution (901 mL) was added, maintaining the temperature below 20° C. A solution of 2,5-difluorobenzyl bromide (355 g, 1.72 mol) in industrial methylated spirits (250 mL) was added dropwise to the thiolate solution, maintaining the temperature below 15° C. Upon completion of the reaction, water (1000 mL) was added. The resulting slurry was aged at 5° C. and then filtered. The cake was washed sequentially with cold industrial methylated spirits: water (40:60) and then water (500 mL). Drying in vacuo at ambient temperature furnished 2-[[(4-chlorophenyl)thio]methyl]-1,4-difluorobenzene (462.3 g, 99.6%). $^1$H NMR (CDCl$_3$)—as obtained for the corresponding intermediate of Method (a).

A mixture of sodium tungstate dihydrate (1.83 g, 5.54mmol) as a solution in water (36.56 mL), 1M sulfuric acid (2.50 mL), 2-[[(4-chlorophenyl)thio]methyl]-1,4-difluorobenzene (Example 1) (100 g, 0.37 mol) and Aliquat 336™ (2.99 g, 7.39 mmol) in toluene (500 mL) was heated to 45° C., and 27.5% aqueous hydrogen peroxide (114.2 mL) was added slowly. The mixture was cooled and the unreacted peroxide was quenched by addition of 20 wt % sodium metabisulfite solution (120 mL). The layers were separated. The organic phase was washed with water (190 mL) and concentrated to a total volume of approximately 200 mL. Heptane (400 mL) was added and the resulting mixture was cooled to 0° C. and filtered. The wet cake was washed with 2:1 heptane:toluene (200 mL) and then heptane (200 mL). The product was dried in vacuo at 40° C. to yield 107.6 g of 2-[[(4-chlorophenyl)sulfonyl]methyl]-1,4-difluorobenzene (96% yield). $^1$H NMR CDCl$_3$—as obtained via Method (a).

Intermediate 2

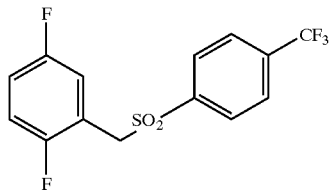

Prepared as for Intermediate 1, using 4-trifluoromethylthiophenol, and obtained as a solid. $^1$H NMR (360 MHz, CDCl$_3$) δ 7.85–7.83 (2H, m), 7.76–7.74 (2H, m), 7.15–7.10 (1H, m), 7.06–7.0 (1H, m), 6.92–6.86 (1H, m) and 4.46 (2H, s).

Preparation 1

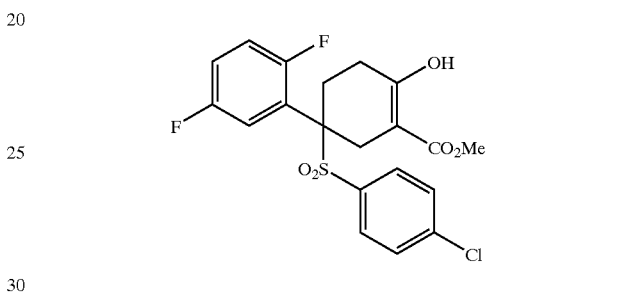

Intermediate 1 (1 g, 3.31 mmol) and methyl acrylate (0.84 ml, 9.27 mmol) in tetrahydrofuran (30 ml) were treated dropwise with potassium $^t$butoxide (3.64 ml 1M solution in tetrahydrofuran, 3.64 mmol). The reaction was stirred for 2 hours, diluted with ethyl acetate (100 ml) and washed with water (50 ml) and brine (50 ml). The organic phase was separated, dried (MgSO$_4$) and evaporated to dryness, and the product purified on silica eluting with hexane-ethyl acetate mixtures.(1.0 g). $^1$H NMR CDCl$_3$ 12.0 (1H,s), 7.41 (4H,s), 7.06–7.0 (2H,m), 6.87–6.81 (1H,s), 3.81 (3H,s), 3.38 (1H, dd, J=3.2,15.8 Hz), 3.02–2.92 (2H,m), 2.52 (1H,dd, J=5.7, 18.5 Hz), 2.3–2.2 (1H,m) and 2.2–2.1 (1H,m).

Preparation 2

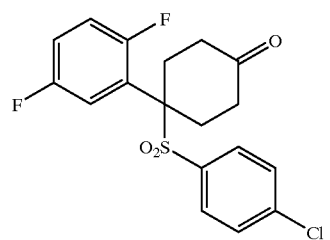

Method (a)

The ester from Preparation 1 (1.0 g, 2.25 mmol) in dimethylsulfoxide (10 ml) was treated with NaCl (0.3 g, 4.96 mmol) and water (0.9 ml, 4.96 mmol) and heated at 150 20° C. for 2 hours. The cooled reaction mixture was diluted with ethyl acetate (100 ml), washed with saturated NH$_4$Cl (100 ml), and the organic phase separated, dried (MgSO$_4$) and evaporated to dryness. The product was purified on silica eluting with hexane-ethyl acetate mixtures, 0.5 g. $^1$H NMR CDCl$_3$ 7.43–7.37 (4H,m), 7.22–7.1 (2H,m), 6.97–6.9 (1H,m), 3.05–2.98 (2H,m) and 2.61–2.53 (2H,m).

Method (b)

(i) 2-[[(4-chlorophenyl)sulfonyl]methyl]-1,4-difluorobenzene (Intermediate 1) (100 g, 0.33 mol) and N,N,N',N'-tetramethyldiaminomethane (34.2 g, 0.50 mol) were dissolved in dimethyl formamide (1000 mL) at 60° C. Acetic anhydride (68.3 g, 1.00 mol) was added slowly and the reaction mixture was aged for 5 hours. Water (1000 mL) was added dropwise and the resulting slurry was cooled to 5° C. The solids were filtered, and the cake washed sequentially with dimethyl formamide:water (40:60, 200 mL) and water (500 mL). Drying overnight in vacuo at 40° C. under a nitrogen stream furnished 2-[1-[(4-chlorophenyl)sulfony]ethenyl]-1,4-difluorobenzene (98 g, 95%). $^1$H NMR (CDCl$_3$) 7.64–7.59 (2H, m), 7.43–7.39 (2H, m), 7.27–7.22 (1H, m), 7.08–6.88 (2H, m), 6.88 (1H, s) and 6.09 (1H, s).

(ii) A solution of 2-[1-[(4-chlorophenyl)sulfonyl]ethenyl]-1,4-difluorobenzene (100 g, 0.32 mol) in xylenes (500 ml) was azeotropically distilled at 38° C., 20 mmHg, until 300 mL solvent had been removed. 2-Trimethylsilyloxybutadiene (90.4 g, 0.64 mol) was then added under a nitrogen atmosphere and the mixture heated to 130° C. After the reaction was completed, the mixture was distilled in vacuo to remove residual diene, whilst maintaining a constant volume by the addition of xylenes (400 mL). The mixture was cooled to 50° C. and THF (500 mL) and 3M HCl (424 mL, 1.27 mol) were added. After the hydrolysis was complete, the layers were separated. The organic layer was washed with water (300 mL) and then concentrated by atmospheric distillation until 350 mL of solvent had been removed. The solution was allowed to cool until crystallisation started, heptane (600 mL) was added and the resulting mixture cooled to ambient. The solids were filtered and washed sequentially with heptane:xylenes (3:1, 200 ml) and then heptane (200 ml). Drying overnight in vacuo at 40° C. furnished 4-[(4-chlorophenyl)sulfonyl]-4-(2,5-difluorophenyl)cyclohexanone (110 g, 90% yield). $^1$H NMR CDCl$_3$—as for the product obtained via Method (a).

Preparation 3

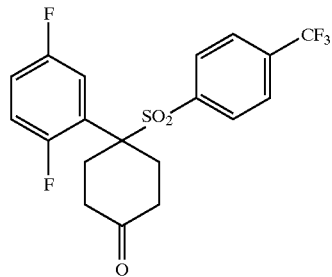

Prepared by the procedures of Preparations 1 and 2 (method (a)) using Intermediate 2 to give the product as a solid. (0.3 g) $^1$H NMR (360 MHz, CDCl$_3$) δ 7.71–7.69 (2H, d, J=7.5 Hz), 6.62–6.60 (2H, d, J=7.4 Hz), 7.22–7.11 (2H, m), 6.95–6.88 (1H, m), 3.02–2.99 (2H, m), 2.63–2.54 (4H, m) and 2.25–2.16 (2H, m).

Preparation 4

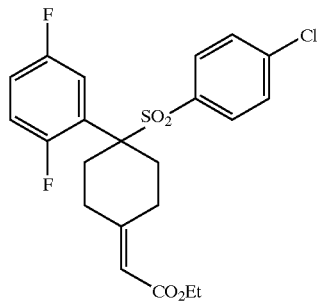

Ethyl (diethoxyphosphinyl)acetate (5.16 mL, 26 mmol) was added dropwise to a slurry of sodium hydride (60% dispersion in mineral oil, 988 mg, 24.7 mmol) in tetrahydrofuran (60 mL) and the mixture was stirred at room temperature for 1 h. The ketone from Preparation 2 (5 g, 13 mmol) in tetrahydrofuran (50 mL) was added dropwise over 20 min. and the mixture was stirred at room temperature for 18 h. Water was added and the mixture was extracted with ethyl acetate. The combined organic fractions were washed with water, dried (MgSO$_4$) and the solvent was evaporated under reduced pressure. The residue was purified by flash column chromatography on silica gel, eluting with isohexane:EtOAc (85:15), to give the product as a white solid (5.2 g, 88%). $^1$H NMR (400 MHz, CDCl$_3$) δ 7.41–7.36 (4H, m), 7.18–7.13 (1H, m), 7.11–7.05 (1H, m), 6.93–6.86 (1H, m), 5.64 (1H, s), 4.14–4.10 (2H, m), 3.99–3.96 (1H, m), 2.91–2.80 (2H, m), 2.42–2.38 (1H, m), 2.31–2.04 (3H, m), 1.89–1.78 (1H, m), 1.28–1.24 (3H, m).

Preparation 5

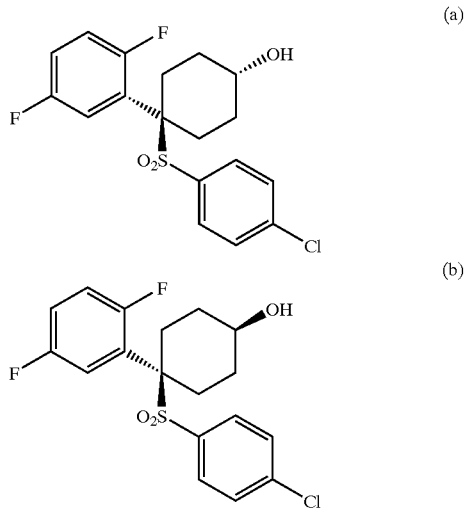

The ketone from Preparation 2, (0.1 g, 0.26 mmol) in methanol (2 ml) was treated with NaBH$_4$ (0.098 g, 0.26 mmol) and stirred for 1 hour. The reaction was quenched with HCl (1N, 10 ml), diluted with ethyl acetate (20 ml), then the organic phase was separated, dried (MgSO$_4$) and evaporated to dryness. The cis and trans products were purified on silica eluting with hexane-ethyl acetate mixtures.

(a) (trans) 0.052 g. ¹H NMR CDCl₃ 7.39–7.33 (4H,m), 7.11–7.02 (2H,m), 6.88–6.82 (1H,m), 3.80–3.73 (1H,m), 2.80–2.60 (2H,m), 2.22–2.16 (2H,m), 2.08–2.04 (2H,m), 1.53(1H,br) and 1.27–1.13 (2H,m). (b) (cis) ¹H NMR (CDCl₃) 7.40 (4H,s), 7.16–7.03 (2H,m), 6.90–6.83 (1H,m), 3.97–3.95 (1H, m), 3.77–3.68 (1H, m), 3.51–3.49 (1H, m), 2.61–2.53 (2H, 1.91–1.83 (2H, m) and 1.50–1.42 (2H, m).

Preparation 6

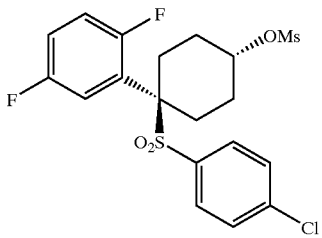

The trans cyclohexanol from Preparation 5 (2.7 g, 6.9 mmol) and triethylamine (1.45 mL, 10.3 mmol) in dichloromethane (50 mL) were treated with methane sulphonyl chloride (0.645 mL, 8.9 mmol) at −30° C. After 30 mins the mixture was washed with water (20 mL), 10% aqueous citric acid (20 mL) and saturated aqueous sodium hydrogen carbonate (50 mL), dried (MgSO₄) and evaporated to dryness. The solid was triturated with ether to give the mesylate (2.6 g) ¹H NMR (CDCl₃) 7.40–7.37 (4H,m), 7.12–7.07 (2H,m), 6.92–6.83 (1H,m), 4.78–4.65 (1H, m), 2.96 (3H, s), 2.88–2.52 (2H, m), 2.29–2.21 (4H, m) and 1.59–1.47 (2H, m).

Preparation 7

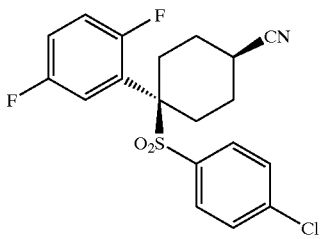

The trans mesylate from Preparation 6 (103 mg, 0.22 mmol) was dissolved in toluene (20 ml) and added to a pre-azeotroped sample of tetrabutylammonium cyanide (354 mg, 1.32 mmol). and the mixture was warmed to 70° C. over 18 hr and then cooled to rt. The solution was diluted with water (10 ml) and washed with ethyl acetate (2×50 ml). The organic phase was washed with brine (10 ml), dried (MgSO₄) and evaporated. The clear oil obtained was purified by column chromatography on silica gel eluting with 10–20% ethyl acetate in hexanes, to give the cyanide. ¹H NMR (CDCl₃) 7.42–7.36 (4H, s), 7.10–7.05 (2H, m), 6.89–6.84 (1H, m), 2.88–2.86 (1H, m), 2.76–2.72 (2H, m), 2.52–2.45 (1H,m), 2.12–2.07 (1H, m) and 1.56–1.49 (1H, m).

Preparation 8

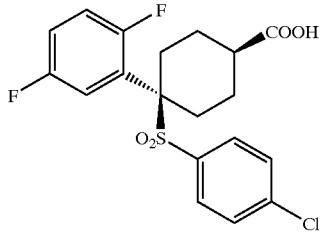

The cyanide from Preparation 7 (143 mg, 0.36 mmol) was dissolved/suspended in a mixture of glacial acetic acid (10 ml) and conc. HCl (6 ml) and heated at 110° C. for 15 hours. The mixture was cooled, diluted with ethyl acetate and washed with water (×3), dried (MgSO₄) and evaporated to dryness. This crude residue (153 mg) was purified by preparative tlc (5% methanol in dichloromethane/1% acetic acid). ¹H NMR (CDCl₃) 7.38–7.35 (4H, s), 7.08–7.06 (2H, m), 6.90–6.84 (1H, m), 2.65–2.58 (2H, m), 2.38–2.33 (3H, m), and 1.75–1.49 (4H, m).

Preparation 9

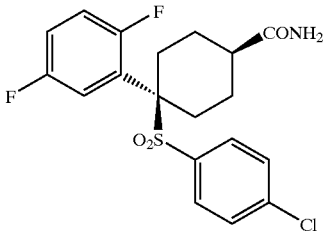

The cyanide from Preparation 8 (50 mg, 0.12 mmol) was dissolved in a mixture of tetrahydrofuran (4.5 ml) and water (0.5 ml) and stirred at 20° C. The mixture was treated with hydrogen peroxide (20 ml, 0.6 mmol) and then with lithium hydroxide (6 mg, 0.25 mmol) for 2 hours. Hydrogen peroxide (20 ml, 0.6 mmol) and then with lithium hydroxide (6 mg, 0.25 mmol) were added and the mixture was stirred at rt. for 72 hrs. The mixture was cooled, diluted with ethyl acetate and washed with water (×2) and sat. sodium bisulphite, dried (MgSO₄) and evaporated to dryness. This crude residue (51 mg) was purified by preparative tlc (20% ethyl acetate in hexanes) ¹H NMR (CDCl₃) 7.37 (4H, s), 7.10–7.02 (2H, m), 6.90–6.84 (1H, m), 5.57 (2H, brs), 2.54–2.48 (3H, m), 2.43–2.39 (1H, m), 2.19–2.15 (2H, m) and 1.62–1.50 (3H, m).

Preparation 10

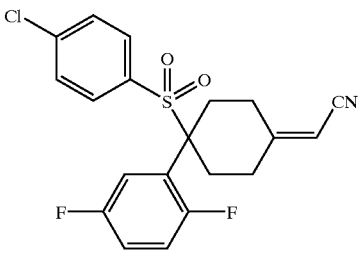

To a solution of potassium tert butoxide (1.0M in THF, 3.20 Kg, 3.55 mol) in tetrahydrofuran (2.1 L) was added diethyl (cyanomethyl)phosphonate (642 g, 3.62 mol), maintaining the temperature below 5° C. The resulting solution was aged for 2 h and a solution of 4-[(4-chlorophenyl)

sulfonyl]-4-(2,5-difluorophenyl)cyclohexanone (1.07 Kg, 2.78 mol) (Preparation 2) in tetrahydrofuran (3.9 L) was added. After the reaction was completed, isopropyl acetate (13.1 L) and water (26.3 L) were added. The organic layer was washed with brine and then concentrated to 1 L. Heptane (10.5 L) was added. The resulting solid was filtered, washed with heptane, dried in vacuo at 37° C. and then slurried in diethyl ether (5 L). Filtration and drying in vacuo afforded 989 g (87% yield) of [4-[(4-chlorophenyl) sulfonyl]-4-(2,5-difluorophenyl)cyclohexylidene] acetonitrile.

$^1$H NMR (CDCl$_3$) 7.41–7.34 (4H, m), 7.25–7.06 (2H, m), 6.94–6.87 (1H, m), 5.12 (1H, s), 3.05–3.03 (1H, m), 2.92–2.86 (2H, m), 2.54–2.50 (1H, m), and 2.30–2.03 (4H, m).

Example 1

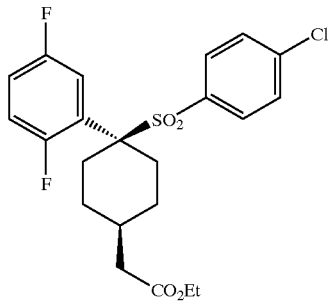

Sodium borohydride (313 mg, 8.23 mmol) was added to a mixture of the unsaturated ester from Preparation 4 (3.74 g, 8.23 mmol) and nickel (II) chloride (2.67 g, 20.6 mmol) in ethanol (100 mL). The mixture was stirred at room temperature for 20 min., then water (100 mL) was added. The mixture was filtered through Hyflo™, washing with ethanol and ethyl acetate. The solvent was evaporated under reduced pressure and the residue was partitioned between ethyl acetate and water. The organic layer was collected, dried (MgSO$_4$) and the solvent was evaporated under reduced pressure. The residue was purified by flash column chromatography on silica gel, eluting with isohexane:EtOAc (85:15), to give the faster running cis-isomer, as an oil (1.36 g, 36%), $^1$H NMR (400 MHz, CDCl$_3$) δ 7.37–7.30 (4H, m), 7.09–7.00 (2H, m), 6.86–6.79 (1H, m), 4.14 (2H, q, J=7.1 Hz), 2.47 (2H, d, J=7.6 Hz), 2.46–2.38 (2H, m), 2.19–2.14 (1H, m), 1.76–1.71 (2H, m), 1.57–1.48 (4H, m), 1.27 (3H, t, J 7.1 Hz); and the slower running trans-isomer, as an oil (200 mg, 5.3%). $^1$H NMR (400 MHz, CDCl$_3$) δ 7.39–7.34 (4H, m), 7.10–7.03 (2H, m), 6.88–6.82 (1H, m), 4.08 (2H, q, J=7.1 Hz), 2.98'2.85 (1H, m), 2.67–2.53 (1H, m), 2.22–2.11 (2H, m), 2.06 (2H, d, J=6.9 Hz), 2.01–1.85 (3H, m), 1.20 (3H, t, J=7.1 Hz), 1.01–0.90 (2H, m).

Example 2

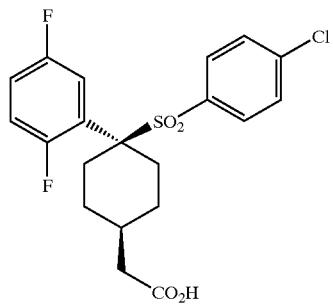

Lithium hydroxide (350 mg, 14.57 mmol) was added to a solution of the cis-ester from Example 1, (1.33 g, 2.91 mmol) in ethanol (40 mL). The mixture was degassed and stirred at room temperature under nitrogen gas for 5 h. The mixture was poured into aqueous hydrochloric acid (1M) and extracted with ethyl acetate. The organic extract was dried (MgSO$_4$) and the solvent was evaporated under reduced pressure to give a white solid which was then crystallized from IPA to give the product as a white solid (950 mg, 76%). $^1$H NMR (400 MHz, CD$_3$OD) δ 7.51–7.49 (2H, m), 7.40–7.37 (2H, m), 7.19–7.10 (2H, m), 7.00–6.94 (1H, m), 2.51–2.35 (6H, m), 2.13–2.10 (1H, m), 1.78–1.74 (2H, m), 1.57–1.50 (2H, m).

Example 3

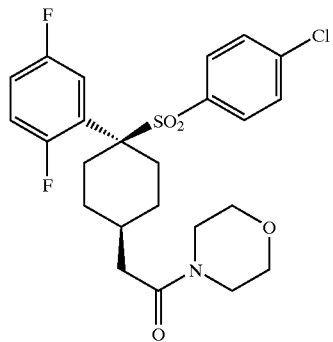

The acid from Example 2 (50 mg, 0.117 mmol), morpholine (30 µL, 0.351 mmol), 1-hydroxybenzotriazole (24 mg, 0.176 mmol) and triethylamine (65 µL, 0.468 mmol) was stirred in tetrahydrofuran at room temperature under nitrogen gas for 10 min. 1-(3-Dimethylaminopropyl)-3-ethylcarbodiimide hydrochloride (45 mg, 0.234 mmol) was added to the mixture and stirred for 24 h. The mixture was poured into aqueous sodium hydroxide (1M) and extracted with ethyl acetate. The organic extract was dried (MgSO$_4$) and the solvent was evaporated under reduced pressure. The residue was purified by flash column chromatography on silica gel, eluting with 5 to 10% methanol in dichloromethane, to give the product as a white foam (50 mg, 86%). $^1$H NMR (400 MHz, CD$_3$OD) δ 7.50 (2H, d, J 8.6 Hz), 7.37 (2H, d, J 8.6 Hz), 7.19–7.09 (2H, m), 7.00–6.93 (1H, m), 3.69–3.63 (4H, m), 3.59–3.56 (4H, m), 2.55 (2H, d, J 7.4 Hz), 2.47–2.39 (4H, m), 2.16–2.07 (1H, m), 1.78–1.74 (2H, m), 1.58–1.51 (2H, m). m/z (ES$^+$) (M+1) 498+500.

Examples 4–15

The following compounds were prepared according to the method of Example 3, using the appropriate amine in place of morpholine.

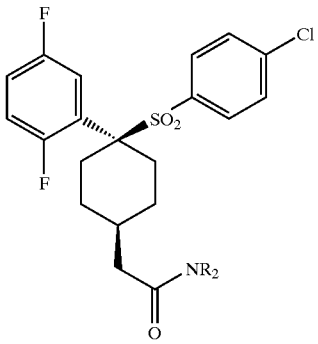

| Ex. | —NR$_2$ | Formula | M.W. | m/z (ES$^+$) (M + 1) |
|---|---|---|---|---|
| 4 | —N(CH$_2$CH$_2$)$_2$N— | C$_{25}$H$_{29}$ClF$_2$N$_2$O$_3$S | 510, 512 | 511, 513 |
| 5 | —N(CH$_2$CH$_2$)$_2$N-Ph | C$_{30}$H$_{31}$ClF$_2$N$_2$O$_3$S | 572, 574 | 573, 575 |
| 6 | piperidine-4-OH | C$_{25}$H$_{28}$ClF$_2$NO$_4$S | 511, 513 | 512, 514 |
| 7 | —NH-CH$_2$CH$_2$-(2-pyridyl) | C$_{27}$H$_{27}$ClF$_2$N$_2$O$_3$S | 532, 534 | 533, 535 |
| 8 | —NH-(CH$_2$)$_3$-imidazolyl | C$_{26}$H$_{28}$ClF$_2$N$_3$O$_3$S | 535, 537 | 536, 538 |
| 9 | piperidine-4-CO$_2$Et | C$_{28}$H$_{32}$ClF$_2$NO$_5$S | 567, 569 | 568, 570 |
| 10 | piperidine-3-CO$_2$Et | C$_{28}$H$_{32}$ClF$_2$NO$_5$S | 567, 569 | 568, 570 |
| 11 | piperidine-3-CO$_2$Et | C$_{28}$H$_{32}$ClF$_2$NO$_5$S | 567, 569 | 568, 570 |
| 12 | piperidine-3-CO$_2$Et | C$_{28}$H$_{32}$ClF$_2$NO$_5$S | 567, 569 | 568, 570 |
| 13 | piperidine | C$_{25}$H$_{28}$ClF$_2$NO$_3$S | 495, 497 | 496, 498 |
| 14 | 3-methyl-piperidine-3-CO$_2$Et | C$_{29}$H$_{34}$ClF$_2$NO$_5$S | 581, 583 | 582, 584 |
| 15 | 3-methyl-piperidine-3-CO$_2$Et | C$_{29}$H$_{34}$ClF$_2$NO$_5$S | 581, 583 | 582, 584 |

Example 16

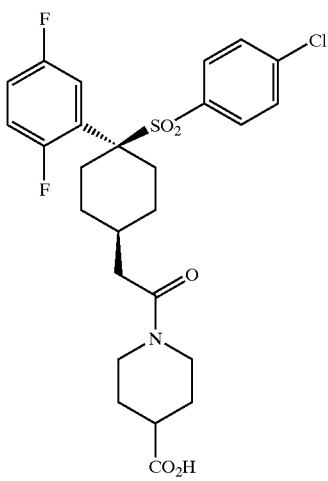

Lithium hydroxide (20 mg, 0.833 mmol) was added to a solution of ester from Example 9 (95 mg, 0.167 mmol) in ethanol (12 ml) and water (4 ml). The mixture was degassed and stirred at room temperature under nitrogen gas for 18 h. The mixture was poured into aqueous hydrochloric acid (1M) and extracted with ethyl acetate. The organic extract was dried (MgSO$_4$) and the solvent was evaporated under reduced pressure to give the product as a white solid (75 mg, 83%). $^1$H NMR (400 MHz, CD$_3$OD) δ 7.50 (2H, d, J 8.6 Hz), 7.38 (2H, d, J 8.6 Hz), 7.19–7.10 (2H, m), 7.00–6.93 (1H, m), 4.37–4.32 (1H, m), 3.98–3.90 (1H, m), 3.26–3.18 (1H, m), 2.90–2.82 (1H, m), 2.64–2.38 (7H, m), 2.10–2.06 (1H, m), 2.00–1.91 (2H, m), 1.78–1.49 (6H, m). m/z (ES$^+$) (M+1) 540+542.

Examples 17–21

The following compounds were prepared according to the method of Example 16 using the appropriate esters from Examples 10–15.

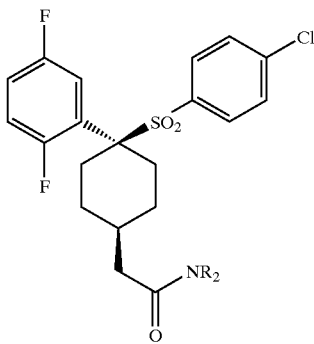

| Ex. | —NR$_2$ | Formula | M.W | m/z (ES$^+$) (M + 1) |
|---|---|---|---|---|
| 17 | -N(piperidine-3-CO$_2$H) | C$_{26}$H$_{28}$ClF$_2$NO$_5$S | 539 / 541 | 540 / 542 |
| 18 | -N(piperidine-3-CO$_2$H) | C$_{28}$H$_{32}$ClF$_2$NO$_5$S | 539 / 541 | 540 / 542 |
| 19 | -N(piperidine-3-CO$_2$H) | C$_{28}$H$_{32}$ClF$_2$NO$_5$S | 539 / 541 | 540 / 542 |
| 20 | -N(piperidine-3-CO$_2$H) | C$_{27}$H$_{30}$ClF$_2$NO$_5$S | 553 / 555 | 554 / 556 |
| 21 | -N(piperidine-3-CO$_2$H) | C$_{27}$H$_{30}$ClF$_2$NO$_5$S | 553 / 555 | 554 / 556 |

Examples 22–39

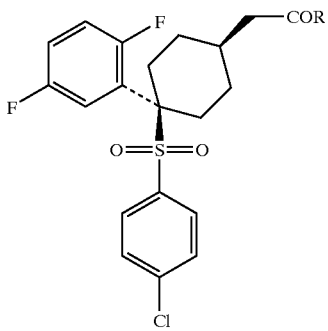

These Examples were prepared by the following method, using the appropriate amine free base or amine salt with prior neutralization.

To a stirred suspension of cis -4-[(4-chlorophenyl)sulfonyl]-4-(2,5-difluorophenyl)cyclohexaneacetic acid (Example 2, 0.15 g, 0.35 mmol) in dichloromethane (5 ml) was added oxalyl chloride (0.05 ml, 0.57 mmol) and dimethylformamide (1 drop). After 30 minutes the solution was evaporated to a small volume and to a solution of the residue in dichloromethane (5 ml) was added the desired amine (1.75 mmol). After stirring the solution for 20 minutes the solvent was removed in vacuo and the residue purified by chromatography on silica gel eluting with increasing concentrations of ethyl acetate in isohexane (25%, 50%). The fractions containing the product were evaporated to give the product amide. Chromatographic purification was performed on silica gel using appropriate concentrations of ethyl acetate in isohexane, ethyl acetate or methanol in ethyl acetate where appropriate.

| Example No. | R | MS m/z (M + H) | m.p. |
|---|---|---|---|
| 22 | NH-cyclobutyl | 482, 484 | 192–193° C. |
| 23 | NH$_2$ | 428, 430 | 187–189° C. |
| 24 | NHMe | 442, 444 | 200–201° C. |
| 25 | NHEt | 456, 458 | 146–147° C. |
| 26 | NH$^n$Pr | 470, 472 | 150–151° C. |
| 27 | NH$^i$Pr | 470, 472 | 124–125° C. |
| 28 | NMe$_2$ | 456, 458 | |
| 29 | NHCH$_2$CH$_2$Ph | 532, 534 | |
| 30 | NHCH$_2$CF$_3$ | 510, 512 | |
| 31 | N(thiomorpholine-S,S-dioxide) | 546, 548 | |
| 32 | NHCH$_2$-cyclopropyl | 482, 484 | 187–188° C. |
| 33 | NH-cyclopentyl | 496, 498 | 182–183° C. |
| 34 | NH-cyclopropyl | 468, 470 | 145–147° C. |
| 35 | NH$^n$Bu | 484, 486 | Oil |
| 36 | NH$^t$Bu | 484, 486 | 102–110° C. |
| 37 | NHCH(Et)$_2$ | 498, 500 | 89–92° C. |
| 38 | NH-allyl | 468, 470 | 132–134° C. |
| 39 | NHNH$^t$Bu | 499, 501 | |

Example 40

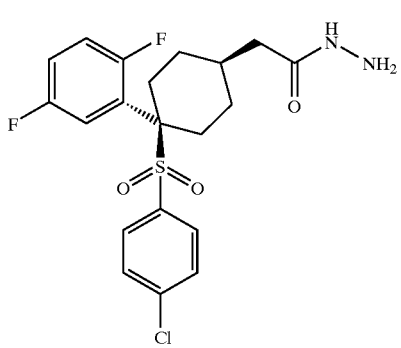

Step (1)

To a solution of the acid from Example 2 (1 g) in DCM (50 ml) and ethyl acetate (30 ml) was added pentafluorophenol (1.5 equiv.) and DCC (1.5 equiv.) and stirred at room temperature for 1 h. The reaction mixture was evaporated in vacuo, taken up in ethyl acetate and filtered. The filtrate was evaporated in vacuo to yield the pentafluorophenol ester of sufficient purity to use in subsequent reactions without further purification.

Step (2)

To the active ester prepared in Step (1) (200 mg, 0.33 mmol) dissolved in dry THF (3 ml) and under nitrogen was added hydrazine (1 M solution in THF, 1.3 ml, 1.32 mmol). After 3 h the reaction was concentrated diluted with water, extracted with ethyl acetate (×3), washed with, water, brine, dried (MgSO$_4$), filtered and evaporated. Purified by flash column chromatography (1:1 $^i$hexane/ethyl acetate to ethyl acetate+3% triethylamine) to give a white solid (50 mg). MS(EI+) 444 (MH+).

Example 41

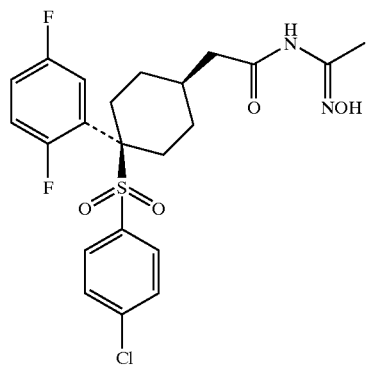

A solution of the active ester from step (1) of Example 40 in DMF was treated with acetamidoxime at room temperature. The reaction mixture was stirred for 0.5 h, diluted with ethyl acetate, washed with water, dried, filtered and evaporated in vacuo. Purification by column chromatography gave the desired product as a white solid (180 mg, 100%). MS MH+ 485(487).

Example 42

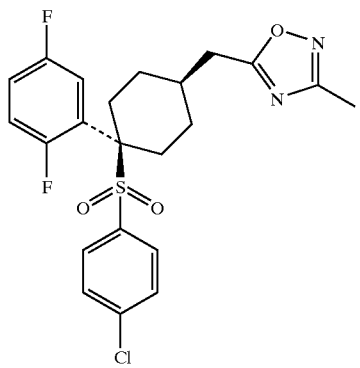

A solution of the oxime from Example 41 (100 mg) in THF (5 ml) was treated with potassium tert-butoxide solution (3 equiv.) and stirred at room temperature for 15 mins. The reaction mixture was diluted with water and ethyl acetate. The organic phase was washed, dried, filtered and evaporated. Purification by column chromatography gave the desired product (65 mg, 62%) as a white solid. MS MH+ 467(469).

Example 43

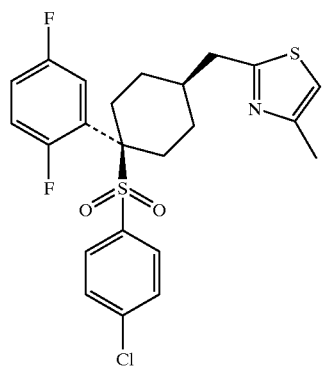

A solution of the amide from Example 23 (100 mg) was dissolved in dioxane and treated with Lawesson's reagent and stirred at room temperature overnight. The reaction mixture was filtered and the filtrate was evaporated in vacuo. Purification by column chromatography gave the thioamide (50 mg, 52%) as a white solid. A solution of the foregoing thioamide (40 mg) in ethanol (2 ml) was treated with chloroacetone (1.3 equiv.) and refluxed for 4 h. The reaction mixture was evaporated in vacuo. Trituration from hexane-ethyl acetate gave the desired product (26 mg, 59%) as a white solid. MS MH+ 482(484).

Example 44

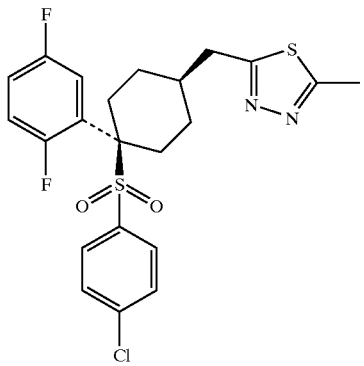

A solution of the active ester from Example 40 step (1) in DMF was treated with acetic hydrazide and stirred at room temperature for 15 min. The reaction mixture was diluted with ether and the precipitate was collected by filtration and washed several times with ether to give the intermediate diacyl hydrazide as a white solid. A solution of the foregoing compound (100 mg) in dioxane was treated with Lawesson's reagent (2 equiv.) and stirred at room temperature for 1 h. The reaction mixture was evaporated in vacuo. Purification by column chromatography gave the desired product (55 mg, 52%) as a white solid. MS MH+ 483(485).

Example 45

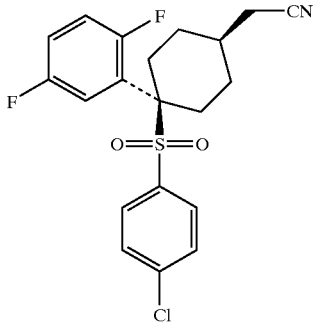

Method (a)

To a solution of the cis amide from Preparation 9 (46 mg) and pyridine (0.053 ml) in tetrahydrofuran (1 ml) was added trifluoroacetic anhydride (0.056 ml). The solution was stirred at room temperature for 2 hours when 0.5M-HCl (aqueous) and ethyl acetate were added. The organic phase was dried (MgSO$_4$), evaporated to a small volume and purified by chromatography on silica gel, eluting with isohexane:ethyl acetate (5:1) to give the desired product as a colourless solid. $^1$H NMR (360 MHz, CDCl$_3$) δ 1.61–1.70 (2H, m), 1.86–1.94 (2H, m), 2.03–2.10 (1H, m), 2.42–2.45 (4H, m), 2.51(2H, d J 8.0 Hz), 6.8 (1H, m), 7.02–7.09(2H, m), 7.30 (2H, d J 8.6 Hz), 7.36(2H, d J 8.7 Hz).

Method (b)

A solution of [4-[(4-chlorophenyl)sulfonyl]-4-(2,5-difluorophenyl)cyclohexylidene]acetonitrile (Preparation 10) (1005 g, 2.5 mol) in tetrahydrofuran (10.1 L) was cooled to –60° C. and L-Selectride™ (1.0M in tetrahydrofuran, 2.50 Kg, 2.81 mol) was added slowly, maintaining the temperature at –60° C. The solution was aged for 60 minutes, warmed to –30° C. and treated with 5M sodium hydroxide (285 mL) and aqueous hydrogen peroxide (27%) (960 mL). Then sodium metabisulphite (95 g) was added at –5° C. and the resulting mixture was allowed to warm to 15° C. The solution was transferred into a mixture of isopropyl acetate (16.7 L), water (15.1 L) and sat. brine (3.7 L). The organic phase was washed with water:sat. brine (1:1, 14 L) and sat. brine (7.3 L). The solution was then concentrated to 1.5 L and heptane (10 L) was added. The resulting solids were filtered and washed with 5% isopropyl acetate in heptane (4 L), then dried under vacuum at 37° C. to afford cis-4-[(4-chlorophenyl)sulfonyl]-4-(2,5-difluorophenyl)cyclohexaneacetonitrile, (970 g, 95% yield).

Example 46

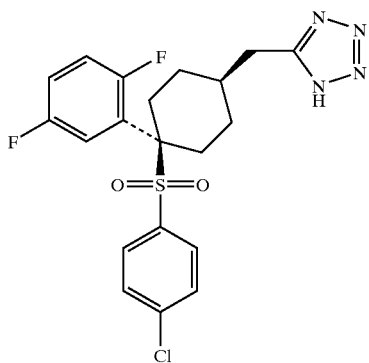

To a solution of the nitrile from Example 45 (0.43 g) in dimethylformamide (0.5 ml) was added ammonium chloride (0.15 g) and sodium azide (0.15 g) and the mixture was heated at 100° C. for 12 h. 0.2M-HCl (5 ml) and ethyl acetate (5 ml) were added and the organic phase was washed with water (5 times) and dried (MgSO$_4$). The solvent was removed in vacuo and the residue was purified by chromatography on silica gel (eluting with ethyl acetate, 5% methanol in ethyl acetate) to give the desired product MS m/z 451 (M–H)

Example 47

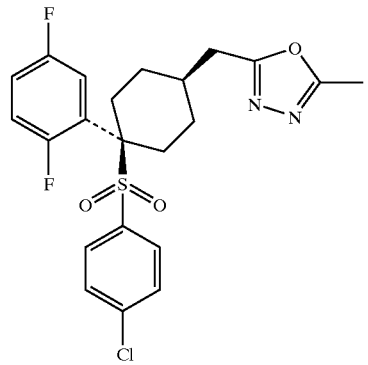

The nitrile from Example 45 (300 mg) was dissolved in methanol (3 ml) and ether (20 ml), cooled to 0° C. and treated with HCl gas for 10 minutes. The reaction vessel was stoppered and left to stand at room temperature overnight. The reaction mixture was evaporated in vacuo to give the imidate ether hydrochloride salt (350 mg, ca 100%) as a white solid.

A solution of the foregoing imidate ether hydrochloride salt (100 mg) in methanol (10 ml) was treated with acetic hydrazide (1.5 equiv.) and stirred at room temperature for 5 min. The reaction mixture was evaporated in vacuo and taken up in Dowtherm A, treated with ammonium chloride (100 mg) and heated at 190° C. for 2 h. The reaction mixture was cooled and purified by column chromatography to give the desired product (24 mg, 24%) as a white solid. MS MH+ 467(469).

Example 48

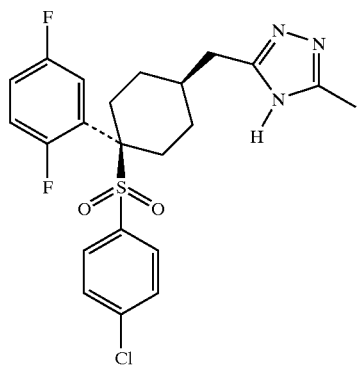

A suspension of the hydrazide of Example 40 (160 mg) in methanol (10 ml) was treated with a solution of acetamidine (2 equiv.) in ethanol (1 ml) and stirred at room temperature overnight, then refluxed for 2 h. The reaction mixture was evaporated in vacuo, dissolved in N-methyl-pyrrolidinone (2 ml) and xylene (30 ml) and refluxed overnight with the azeotropic removal of water. The reaction mixture was evaporated in vacuo, dissolved in ethyl acetate and washed with water (three times). The organic phase was dried, filtered and evaporated. Purification by column chromatography gave the desired product (137 mg, 76%) as a white solid. MS MH+ 466(468).

Example 49

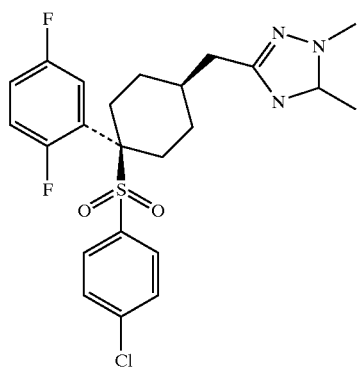

A solution of the triazole from Example 48 (50 mg) in DMF (1 ml) was treated with sodium hydride (1.1 equiv.) and, after 5 minutes, methyl iodide (1.5 equiv.). After 1 h, the reaction mixture was diluted with ethyl acetate and water. The organic layer was washed with water, dried, filtered and evaporated in vacuo. Purification by column chromatography gave the desired product (33 mg, 64%) as a white foam. $^1$H NMR indicated this compound to be a mixture of N1/N2 methylated regioisomers. MS MH+ 480 (482).

Example 50

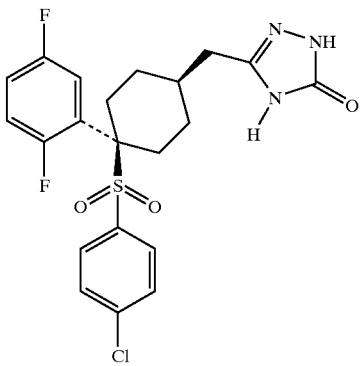

A solution of the active ester from Example 40 step (1) (200 mg) in toluene was treated with a suspension of semicarbazide hydrochloride (1.1 equiv.) in DMF and triethylamine (2.2 equiv.) and stirred at room temperature for half an hour. The reaction mixture was diluted with ether and filtered. The residue was washed with ether to give the crude acyl semicarbazide as a white solid.

A suspension of this material (150 mg) in 1 M NaOH solution (20 ml) and a small amount of 1,4-dioxane was refluxed overnight. The reaction mixture was cooled and acidified with 1 M HCl. The resulting precipitate was collected by filtration, washed with water and ether several times and dried in vacuo to give the desired product as a white solid. MS MH+ 468(470).

Example 51

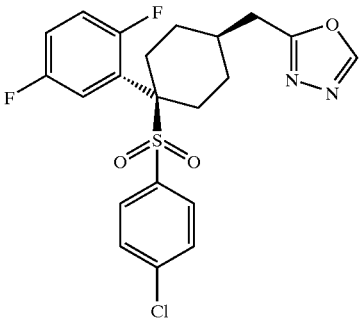

The hydrazide prepared in Example 40 (40 mg, 0.09 mmol) was dissolved in triethyl orthoformate (3 ml) and heated at 150° C. for 18 h. Reaction was concentrated and purified by flash chromatography (1:1 $^i$hexane/ethyl acetate) to give a colourless glassy solid (12 mg). $^1$H NMR (CDCl$_3$) 1.55–1.62 (2H, m), 1.77–1.82 (2H, m), 2.20–2.28 (1H, m), 2.44 (1H, s), 2.50 (3H, dd, J=5.5, 14.5 Hz), 3.07 (2H, d, J=7.8 Hz), 6.80–6.87 (1H, m), 7.01–7.09 (2H, m), 7.31–7.38 (4H, m), 8.36 (1H, s).

Example 52

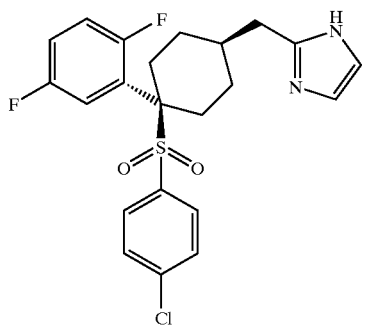

To the acid prepared in Example 2 (1.0 g, 2.3 mmol) dissolved in THF (80 ml) under nitrogen and cooled to 0° C. were added triethylamine (0.4 ml, 2.8 mmol) and isobutylchloroformate (0.36 ml, 2.8 mmol). Reaction was stirred at 0° C. for 2 h and then the solid in the reaction mixture was removed by filtration. The filtrate was recooled to 0° C. and sodium borohydride (435 mg) in water (10 ml) added dropwise and the reaction was stirred for 1 h. Reaction was concentrated, diluted with ethyl acetate, washed with water, brine, dried (MgSO$_4$), filtered and evaporated. Purified by flash chromatography (1:1 $^i$hexane/ethyl acetate) to give the alcohol (0.96 g).

To the alcohol (400 mg, 0.97 mmol) dissolved in DCM (20 ml) was added Dess-Martin periodinane (453 mg, 1.1 mmol). Reaction stirred for 1 h and then filtered through a pad of Celite™ and the filtrate evaporated and the residue purified by flash chromatography (2:1 $^i$hexane/ethyl acetate) to give the aldehyde (250 mg) which was dissolved in ethanol (5 ml), cooled to 0° C. and treated with glyoxal (40% w/w aq solution, 0.2 ml) and ammonia (25% w/w aq. solution, 1 ml). After 30 min the reaction was allowed to warm to room temperature and stirred for 15 h. After concentration the residue was diluted with brine and extracted with ethyl acetate (×3). Organic extracts were dried (MgSO$_4$), filtered and evaporated to give the imidazole as a white solid (150 mg). $^1$H NMR (CDCl$_3$) 1.45–1.55 (2H, m), 1.70–1.75 (2H, m), 2.17–2.22 (1H, m), 2.46 (4H, dd, J=5.6, 14.0 Hz), 2.88 (2H, d, J=7.7 Hz), 6.78–6.85 (1H, m), 6.98 (2H, s), 7.00–7.05 (2H, m), 7.31–7.36 (4H, M), 9.1–9.8 (1H, br).

Example 53

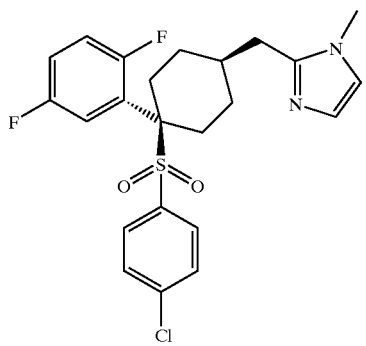

The imidazole prepared in Example 52 (35 mg, 0.078 mmol) was dissolved in dry DMF (2 ml) and treated with potassium carbonate (53 mg, 0.39 mmol) and iodomethane (6 µl, 0.096 mmol) and allowed to stir for 48 h. The reaction was diluted with water and extracted with ethyl acetate (×3). Organic extracts were dried (MgSO$_4$), filtered and evaporated and purified by flash chromatography (ethyl acetate) to give a white solid (8 mg). $^1$H NMR (CDCl$_3$) 1.51–1.59 (1H, m), 1.80 (4H, dd, J=3.9, 10.5 Hz), 2.19–2.26 (1H, m), 2.42–2.57 (3H, m), 2.80 (2 H, d, J=7.7 Hz), 3.60 (3 H, s), 6.79 (1 H, d, J=1.1 Hz), 6.81–6.86 (1 H, m), 6.94 (1H, d, J=1.4 Hz), 7.00–7.08 (2H, m), 7.34 (4H, d, J=4.2 Hz).

Example 54

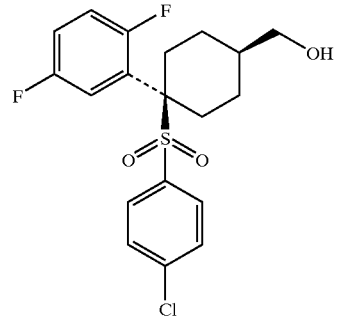

The acid from Preparation 8 (153 mg) was dissolved in dry THF (10 ml) and cooled to 0° C. under nitrogen. Triethylamine (61 µL, 0.43 mmol) and isobutylchloroformate (57 µL, 0.43 mmol) were added and the mixture stirred at 0° C. for one hour. The precipitate that had formed was removed by filtration and washed with a further 5 ml of dry THF. The combined THF layers were recooled to 0° C. and sodium borohydride (70 mg, 1.84 mmol) as a solution in water (2 ml) was added with effervescence. After stirring for 30 minutes at 0° C., the reaction was diluted with ethyl acetate, washed with ammonium chloride solution, sodium bicarbonate solution and brine then dried (MgSO$_4$) and evaporated to dryness. The residue was purified by column chromatography eluting with ethyl acetate:hexane (1:3) to afford the desired alcohol (75 mg). $^1$H NMR (CDCl$_3$) 7.39–7.31 (4H, m), 7.10–7.01 (2H, m), 6.88–6.81 (1H, m), 3.71 (2H, d, J=7.5 Hz), 2.46–2.32 (4H, m), 1.90–1.85 (2H, m), 1.78–1.74 (1H, m) and 1.54–1.44 (2H, m). m/z=423 [MNa]$^+$.

Example 55

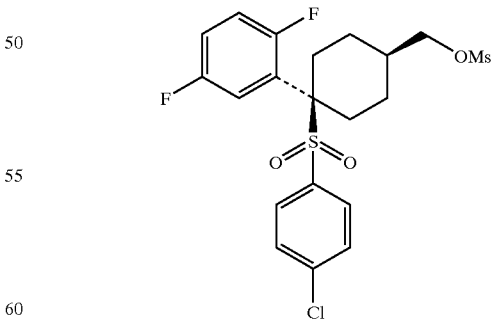

A stirred solution of the alcohol from Example 54 (294 mg, 0.74 mmol) in DCM (10 ml) was cooled to −30° C. Triethylamine (155 µl, 1.11 mmol) then methanesulfonyl chloride (68 µl, 0.89 mmol) were added and the mixture stirred for 30 minutes at −30° C. The reaction was diluted with water, warmed to ambient temperature and extracted with DCM. The organic layer was washed with citric acid solution and sodium bicarbonate solution, dried (MgSO$_4$) and evaporated to dryness. The residue (321 mg) could be used without further purification or purified by column chromatography eluting with ethyl acetate:hexane (1:3) to remove small quantities of the trans isomer to afford the desired product. (272 mg).

$^1$H NMR (CDCl$_3$) 7.36 (2H, d, J=8.5 Hz), 7.31 (2H, d, J=8.5 Hz), 7.08–7.02 (2H, m), 6.87–6.83 (1H, m), 4.29 (1H, d, J=7.5 Hz), 3.05 (3H, s), 2.46–2.42 (4H, m), 2.05–2.02 (1H, m), 1.93–1.88 (2H, m) and 1.62–1.55 (2H, m). m/z=501 [MNa]$^+$.

Example 56

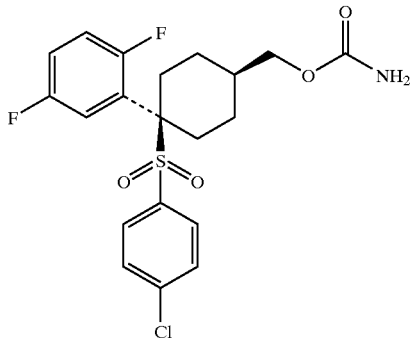

To a stirred solution of the alcohol from Example 54 (59 mg, 0.15 mmol) in dry THF (5 ml) cooled to 0° C. under nitrogen was added chlorosulfonyl isocyanate (18 µl, 0.21 mmol). The mixture was stirred for 45 minutes at this temperature then sodium metabisulfite (84 mg, 0.44 mmol) as a solution in water (1 ml) was added and stirring continued for 16 hours at room temperature. Ethyl acetate was added and the mixture washed with water (×2), brine, dried (MgSO$_4$) and evaporated to leave a residual solid (73 mg) which was triturated with ether and filtered to afford the desired product (35 mg). $^1$H NMR (DMSO) 7.61 (2H, d, J=8.5 Hz), 7.36 (2H, d, J=8.5 Hz), 7.35–7.30 (1H, m), 7.25–7.10 (2H, m), 6.47 (2H, br s), 3.95 (2H, d, J=7.5 Hz), 3.16 (1H, m), 2.44 (1H, m), 2.23–2.14 (2H, m), 1.85–1.67 (3H, m) and 1.38–1.26 (2H, m). m/z=444 [MH]$^+$.

Example 57

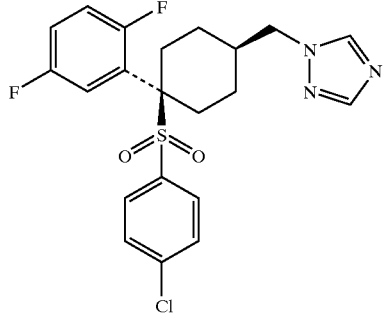

A stirred solution of 1,2,4-triazole sodium derivative (95 mg, 1.04 mmol) in DMSO (5 ml) and the mesylate from Example 55 (100 mg, 0.21 mmol) were heated to 100° C. for 17 hours. The reaction was cooled, diluted with dichloromethane and washed with water, brine (×2), dried (MgSO$_4$) and evaporated to leave a residue which was purified by preparative thin layer chromatography eluting with ether:dichloromethane 1:1 to afford the desired product. $^1$H NMR (CDCl$_3$) 8.09 (1H, s), 7.95 (1H, s), 7.36 (2H, d, J=8.5 Hz), 7.31 (2H, d, J=8.5 Hz), 7.07–7.02 (2H, m), 6.85–6.81 (1H, m), 4.27 (2H, d, J=8 Hz), 2.58–2.39 (4H, m), 2.28–2.22 (1H, m), 1.75–1.68 (2H, m) and 1.6–1.48 (2H, m). m/z=452 [MH]$^+$.

Example 58

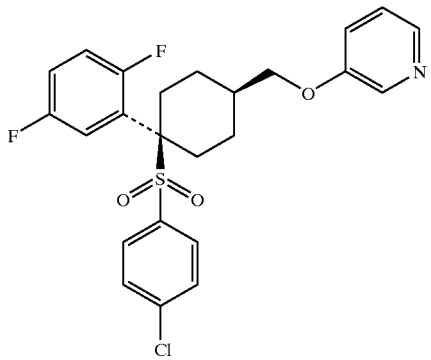

To a stirred solution of the alcohol from Example 54 (114 mg, 0.29 mmol) in dry THF (10 ml) was added 3-hydroxypyridine (30 mg, 0.32 mmol), triphenylphosphine (164 mg, 0.63 mmol) and diethylazodicarboxylate (55 µl, 0.35 mmol) and the resulting solution stirred at ambient temperature for 20 hours. The mixture was evaporated and purified by column chromatography eluting with ethyl acetate:hexane (1:1) to afford the desired product. (52 mg). $^1$H NMR (CDCl$_3$) 8.33 (1H, s), 8.24 (1H, s), 7.37–7.30 (4H, m), 7.25–7.20 (2H, m), 7.11–7.03 (2H, m), 6.88–6.82 (1H, m), 4.07 (2H, d, J=7.5 Hz), 2.50–2.43 (4H, m), 2.13–2.09 (1H, m) 2.01–1.96 (2H, m) and 1.67–1.56 (2H, m). m/z=478[MH]$^+$.

Example 59

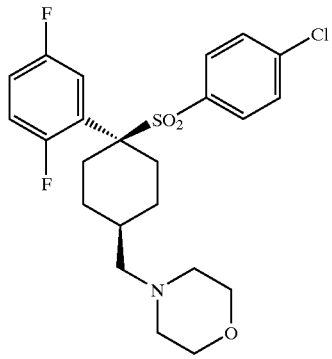

Morpholine (91µL, 1.04 mmol) was added to a solution of the cis-mesylate from Example 55 (50 mg, 0.104 mmol) in acetonitrile (2 mL) and the mixture was stirred at 80° C. for 3 days. The mixture was cooled and the solvent was evaporated under reduced pressure and the residue was dissolved in ethyl acetate. The mixture was washed with aqueous sodium hydroxide (1M), dried (MgSO$_4$) and the solvent was evaporated under reduced pressure. The residue was purified by flash column chromatography on silica gel, eluting with isohexane:EtOAc (1:1), to give the product as a white foam (30 mg, 61%). $^1$H NMR (360 MHz, CD$_3$OD) δ 7.51–7.48 (2H, m), 7.44–7.38 (2H, m), 7.19–7.09 (2H, m), 7.00–6.93 (1H, m), 3.70–3.67 (4H, m), 2.56–2.24 (10H, m), 1.85–1.81 (3H, m), 1.50–1.42 (2H, m).

Example 60

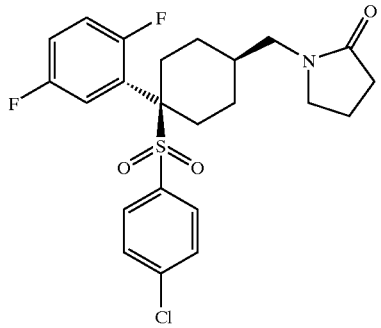

To a stirred solution of pyrrolidin-2-one (23 mg, 0.27 mmol) in DMF (10 ml) under nitrogen was added sodium hydride (11 mg of a 60% dispersion in mineral oil, 0.27 mmol) and the mixture stirred at ambient temperature for 20 minutes. After this time, a solution of the mesylate from Example 55 (44 mg, 0.9 mmol) in DMF (2 ml) was added and the mixture heated to 80° C. for 4 hours. The reaction was cooled, diluted with ethyl acetate and washed with ammonium chloride solution, sodium bicarbonate solution, brine, dried (MgSO$_4$) and evaporated to leave a residue which was purified by preparative thin layer chromatography eluting with ethyl acetate:hexanes 3:1 to afford the desired product (9 mg).

$^1$H NMR (CDCl$_3$) 7.37 (4H, s), 7.08–7.00 (2H, m), 6.88–6.81 (1H, m), 3.38–3.34 (4H, m), 2.51–2.38 (6H, m), 2.06–1.98 (2H, m), 1.92–1.87 (1H, m), 1.70–1.64 (2H, m) and 1.51–1.42 (2H, m). m/z=292[M–ArSO$_2^-$]$^+$.

Using the general procedure of Example 60, and substituting the appropriate nucleophile for pyrrolidin-2-one, the following were prepared:

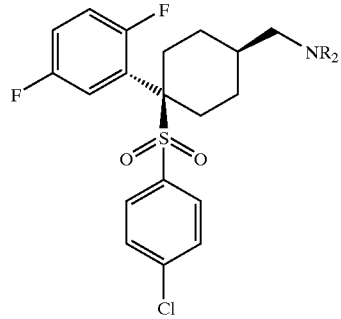

| Example No. | NR$_2$ | m/z |
|---|---|---|
| 61 | (3-methyl-oxazolidin-2-one) | 294 [M-ArSO$_2^-$]$^+$ |
| 62 | (1-methyl-imidazolidin-2-one) | 292 [M-ArSO$_2^-$]$^+$ |
| 63 | (1-methyl-pyrazole) | 275 [M-ArSO$_2^-$]$^+$ 451 [MH]$^+$ |
| 64 | (2-methoxy-pyridine) | 302 [M-ArSO$_2^-$]$^+$ 478 [MH]$^+$ |
| 65 | (1,3-dimethyl-hydantoin) | 321 [M-ArSO$_2^-$]$^+$ 497 [MH]$^+$ |
| 66 | (1-methyl-hydantoin) | 307 [M-ArSO$_2^-$]$^+$ 483 [MH]$^+$ |
| 67 | (3,5,5-trimethyl-oxazolidine-2,4-dione) | *** |
| 68* | (1-methyl-1,2,3-triazole) | 452 [MH]$^+$ |
| 69* | (2-methyl-1,2,3-triazole) | 452 [MH]$^+$ |
| 70 | (1-methyl-imidazole) | 451 [MH]$^+$ |

-continued

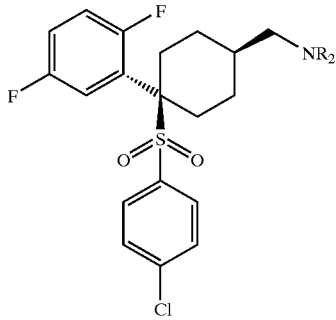

| Example No. | NR₂ | m/z |
|---|---|---|
| 71** | (1-methyl-tetrazol-5-yl) | 453 [MH]⁺ |
| 72** | (2-methyl-tetrazol-5-yl) | 453 [MH]⁺ |
| 73 | (N-methyl-succinimide) | 482 [MH]⁺ |

*obtained as a mixture using 1,2,3-triazole as nucleophile, and separated by preparative TLC (2:1 DCM/hexane 2% MeOH).
**obtained as a mixture using 1,2,3,4-tetrazole as nucleophile, and separated by preparative TLC.
***¹H NMR (CDCl₃) 7.36 (4H, br s), 7.06–7.04 (2H, m), 6.89–6.80 (1H, m), 3.64–3.62 (2H, d, J=7.5Hz), 2.53–2.46 (4H, m), 2.04–2.01 (1H, m), 1.69–1.68 (2H, m) and 1.51–1.50 (2H, m).

Example 74

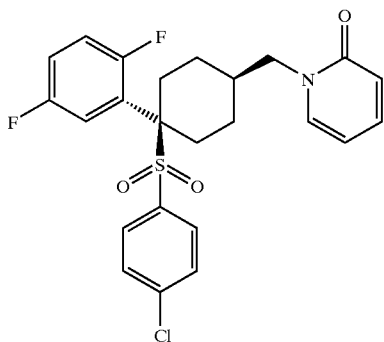

A stirred solution of 2-hydroxypyridine (60 mg, 0.63 mmol) in DME (4 ml) and DMF (1 ml) under nitrogen was cooled to 0° C. Sodium hydride (28 mg of a 60% dispersion in mineral oil, 1.15 mmol) was then added and the suspension stirred at 0° C. LiBr (109 mg, 1.26 mmol) was added 10 minutes later. After this time, the mixture was warmed to ambient temperature and stirred for 15 minutes. A solution of the mesylate from Example 55 (60 mg, 0.13 mmol) in DMF (2 ml) was added and the mixture heated to 65° C. for 18 hours. The reaction was cooled, diluted with ethyl acetate and washed with ammonium chloride solution, sodium bicarbonate solution and brine then dried (MgSO₄) and evaporated to leave a residue which was purified by preparative thin layer chromatography eluting with EtOAc:Hexane 1:5 to afford the desired product (4 mg).

¹H NMR (CDCl₃) 7.55–7.30 (5H, m), 7.25–7.22 (1H, dd J=7.0, 2.0 Hz), 7.09–7.00 (2H, m), 6.85–6.78 (1H, m), 6.58–6.55 (1H, d, J=9.0 Hz), 6.18–6.14 (1H, m), 4.02–3.99 (2H, d, J=8.0 Hz), 2.62–2.55 (2H, m), 2.44 (2H, m), 2.19–2.17 (1H, m), 1.80–1.76 (2H, m) and 1.6–1.5 (2H, m).

Example 75

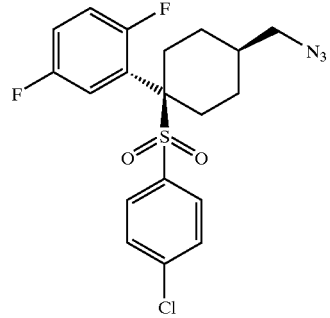

To a stirred solution of the mesylate from Example 55 (9 mg, 0.19 mmol) in DMF (10 ml) under nitrogen was added sodium azide (49 mg, 0.76 mmol) and the mixture stirred and heated to 100° C. for 2 hours. After this time, the reaction was cooled, diluted with water and extracted with ethyl acetate (×2), the combined organic layers were washed with water, dried (MgSO₄) and evaporated to leave a residue (76 mg) which was purified by preparative thin layer chromatography eluting with 4% EtOAc:Hexane to afford the desired product.

¹H NMR (CDCl₃) 7.38–7.30 (4H, m), 7.09–7.01 (2H, m), 6.87–6.80 (1H, m), 3.43–3.41 (2H, d, J=8.0 Hz), 2.46–2.35 (4H, m), 1.87–1.79 (3H, m), 1.56–1.50 (2H, m).

Example 76

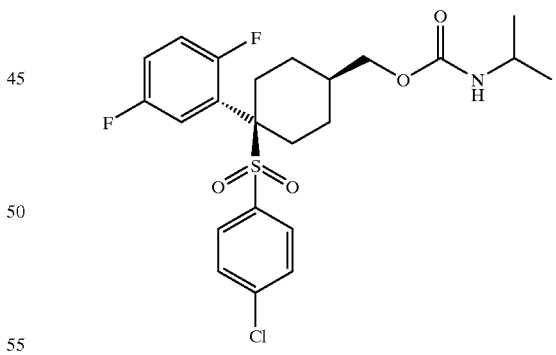

Step (1)

The alcohol from Example 54 (181 mg, 0.46 mmol) was dissolved in THF and pyridine (37 μl, 0.46 mmol) added followed by 4-nitrophenyl chloroformate (103 mg, 0.51 mmol). The reaction was stirred overnight at room temperature then the solvent removed in vacuo and the reaction taken up in ether and washed with water (×2) and brine (×2), dried (MgSO₄) and evaporated to a foam (247 mg). Product was purified by flash column chromatography (1% MeOH, 99% DCM) to yield the desired 4-nitrophenylcarbonate (230 mg)

Step (2)

The carbonate (74 mg, 0.14 mmol) was dissolved in DMF (2 ml) and isopropylamine (23 μl, 0.28 mmol) added. The reaction was stirred for 10 minutes then diluted with ethyl acetate and washed with 2N NaOH (×3) and brine (×3), dried (MgSO$_4$) and evaporated to dryness. The crude product was purified by prep plate (2:1 hexane:ethyl acetate) affording the desired product (18 mg). $^1$H NMR (CDCl$_3$) 7.38–7.30 (4H, m), 7.09–6.99 (2H, m), 6.88–6.79 (1H, m) 4.57–4.48 (1H, s, broad), 4.13 (2H, d, J=8.5 Hz), 3.88–3.71 (1H, m), 2.49–2.38 (4H, m), 1.92–1.80 (3H, m) 1.55–1.41 (2H, m), and 1.16 (6H, d, J=6.5 Hz).

Example 77

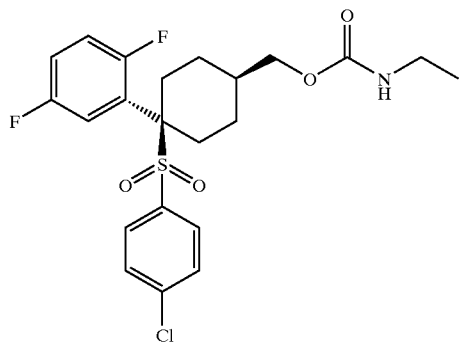

The carbonate from Example 76 step (1) (56 mg, 0.14 mmol) was dissolved in THF (2 ml) and ethylamine (0.4 ml, 0.28 mmol, 2M solution in THF) added. The reaction was stirred for 10 minutes then evaporated to a foam. The reaction was taken up in ethyl acetate and washed with 2N NaOH (×3) and brine (×3), dried (MgSO$_4$) and evaporated to dryness. The crude product was purified by prep plate (2:1 hexane:ethyl acetate) affording the desired product (18 mg). $^1$H NMR (CDCl$_3$) 7.38–7.30 (4H, m), 7.09–6.99 (2H, m), 6.88–6.79 (1H, m) 4.61–4.70 (1H, s, broad), 4.14 (2H, d, J=7 Hz), 3.28–3.15 (2H, m), 2.49–2.38 (4H, m), 1.90–1.79 (3H, m) 1.55–1.42 (2H, m) and 1.15 (3H, t, J=7 Hz).

Example 78

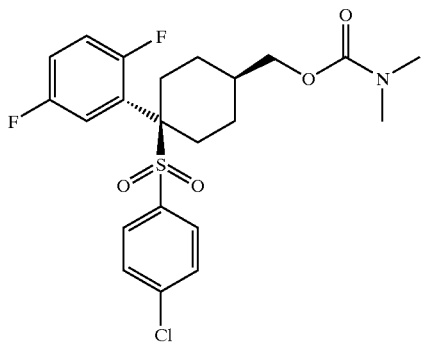

Prepared as for Example 77 using dimethylamine (2M solution in THF) as starting material. Yield 7 mg. $^1$H NMR (CDCl$_3$) 7.38–7.30 (4H, m), 7.09–6.99 (2H, m), 6.88–6.78 (1H, m), 4.15 (2H, d, J=7 Hz), 2.91 (6H, s), 2.49–2.38 (4H, m), 1.95–1.80 (3H, m) and 1.55–1.48 (2H, m).

Example 79

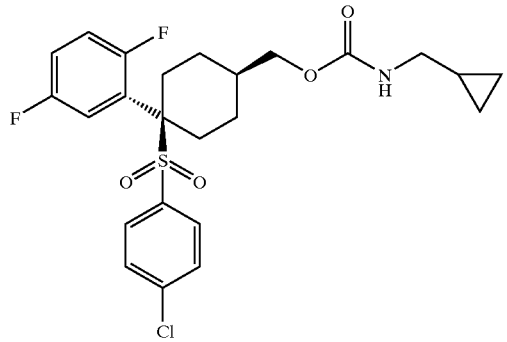

Prepared as for Example 77 using cyclopropylmethylamine as starting material. Yield 11 mg. $^1$H NMR (CDCl$_3$) 7.38–7.30 (4H, m), 7.09–7.00 (2H, m), 6.88–6.78 (1H, m), 4.874.75 (1H, s, broad), 4.14 (2H, d, J=7 Hz), 3.08–2.97 (2H, m), 2.47–2.38 (4H, m), 1.98–1.79 (3H, m), 1.55–1.41 (2H, m), 1.0–0.88 (1H, m), 0.53–0.46 (2H, m) and 0.20–0.12 (2H, m).

Example 80

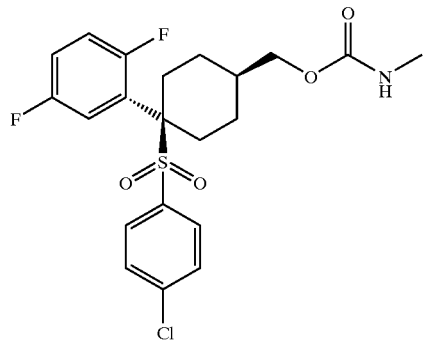

Prepared as for Example 77 using methylamine (8M solution in EtOH) as starting material. Yield 7 mg. $^1$H NMR (CDCl$_3$) 7.38–7.30 (4H, m), 7.09–7.00 (2H, m), 6.88–6.78 (1H, m), 4.68–4.56 (1H, s, broad), 4.14 (2H, d, J=7 Hz), 2.81 (3H, d, J=4.89), 2.48–2.38 (4H, m), 1.91–1.76 (3H, m) and 1.56–1.41 (2H, m).

Example 81

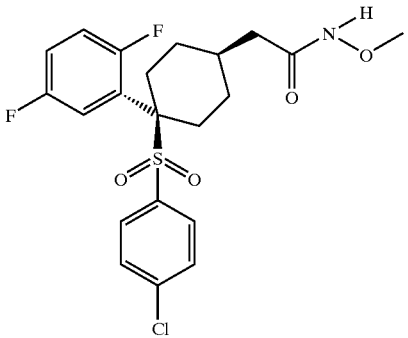

To the pentafluorophenol ester prepared in Example 40 step (1) (140 mg, 0.23 mmol) dissolved in DCM (3 ml) and under nitrogen were added methoxyamine hydrochloride (80 mg, 0.92 mmol) and triethylamine (0.1 ml). After 1 h the reaction was concentrated, diluted with ethyl acetate, washed with aq. sodium carbonate, water, brine, dried (MgSO$_4$), filtered and evaporated. Purified by flash column chromatography (1:1 $^i$hexane/ethyl acetate to ethyl acetate/methanol) to give a white solid (50 mg). $^1$H NMR (CDCl3) 1.56 (2H, br), 1.76 (2H, br), 2.25 (4H, br), 2.44 (4H, br), 3.78 (3H, s), 6.78–6.86 (1H, m), 7.01–7.06 (2H, m), 7.29–7.37 (4H, m).

Example 82

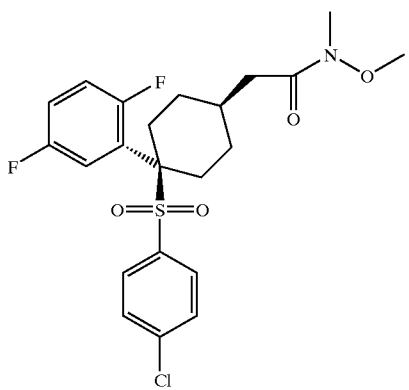

To a stirred suspension of cis -4-[(4-chlorophenyl)sulfonyl]-4-(2,5-difluorophenyl)cyclohexaneacetic acid (Example 2, 0.224 g, 0.52 mmol) in dichloromethane (5 ml) was added oxalyl chloride (0.075 ml, 0.86 mmol) and dimethylformamide (1 drop). After 30minutes the solution was evaporated to a small volume and to a solution of the residue in dichloromethane (5 ml) was added N,O-dimethylhydroxylamine hydrochloride (0.068 g, 0.58 mmol) and diisopropylethylamine (0.2 ml, 1.14 mmol). After stirring the solution for 30 minutes the solvent was removed in vacuo and the residue purified by chromatography on silica gel eluting with increasing concentrations of ethyl acetate in isohexane (33%, 50%). The fractions containing the product were evaporated to give the desired product as a foam. $^1$H NMR (360 MHz, CDCl$_3$) 6 1.50–1.56 (2H, m), 1.72–1.77 (2H, m), 2.24 (1H, m), 2.44 (4H, m),2.57 (2H, d J 7.3 Hz), 3.2 (3H, s),3.7 (3H, s), 6.80–6.88 (1H, m), 7.01–7.08 (2H, m), 7.31 (2H, dd J 6.7 Hz and 2.3 Hz), 7.36 (2H, dd J 6.7 Hz and 2.3 Hz).

Example 83

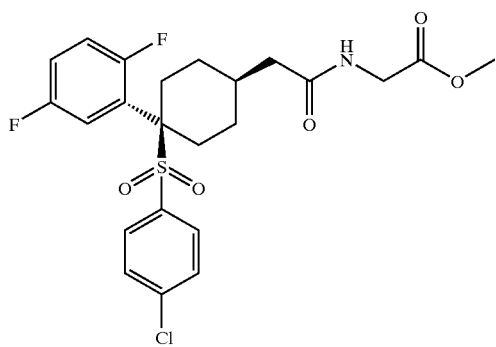

To the pentafluorophenol ester prepared in Example 40 step (1) (155 mg, 0.25 mmol) dissolved in DMF (3 ml) and under nitrogen were added glycine methyl ester hydrochloride (125 mg, 1.0 mmol) and triethylamine (0.15 ml). After 2 h the reaction was diluted with water, extracted with ethyl acetate (×3), washed with, water, brine, dried (MgSO$_4$), filtered and evaporated. Purified by flash column chromatography (1:1 $^i$hexane/ethyl acetate to 9:1 ethyl acetate/methanol) to give a white solid (55 mg). $^1$H NMR (CDCl$_3$) 1.08–1.16 (1H, m), 1.30–1.37 (1H, m), 1.67–1.71 (1H, m), 1.75–1.79 (2H, m), 1.91–1.95 (1H, m), 2.20–2.26 (1H, m), 2.41 (4 H, d, J=7.8 Hz), 3.77 (3H, s), 4.05 (2H, d, J=5.1 Hz), 6.19 (1H, br), 6.79–6.85 (1H, m), 7.00–7.07 (2H, m), 7.30–7.37 (4H, m).

Example 84

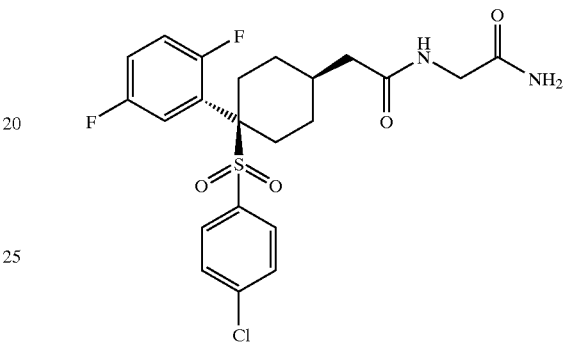

The glycine ester prepared in Example 83 (50 mg, 0.1 mmol) in a sealed tube and dissolved in a 2M ammonia in methanol solution (3 ml) was heated to 50° C. for 3 h. After cooling to room temperature the reaction mixture was concentrated and purified by trituration with ether to give a white solid (28 mg). MS(EI+): 485 (MH+)

Example 85

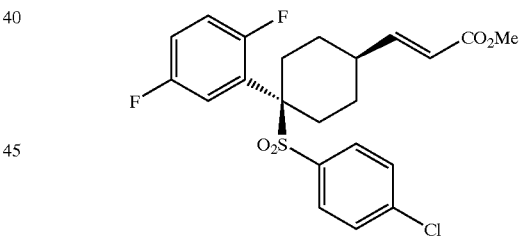

The alcohol from Example 54 (4 g, 10 mmol) was dissolved in dichloromethane (280 ml) and was treated with Dess Martin periodinane (4.66 g, 11 mmol) and the mixture was stirred for 45 mins before adding saturated aqueous sodium bisulphite (100 ml) and after 5 mins the mixture was separated and the organic phase as washed with saturated aqueous sodium bicarbonate (100 ml) dried (MgSO$_4$) and evaporated to dryness. The crude residue (4 g) was dissolved in dry dichloromethane (100 ml) and treated with methyl triphenylphosphinoacetate (4.7 g 14 mmol), stirring at rt. for 16 hrs. The solvent was evaporated and the residue was purified by column chromatography on silica gel eluting with 10–20% ethyl acetate in hexanes, to give the product. $^1$H NMR (CDCl$_3$) 7.37–7.36 (4H, m), 7.10–7.02 (3H, m), 6.87–6.83 (1H, m),5.91 (1H, d, J=16 Hz), 3.77 (3H, s), 2.55–2.45 (3H, m), 2.40–2.38 (2H, m), 1.95–1.90 (2H,m) and 1.65–1.52 (2H, m).

Example 86

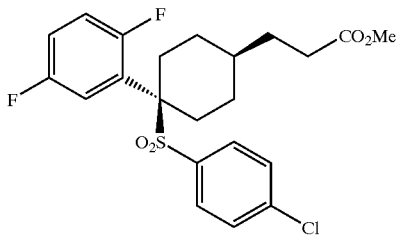

The alkene from Example 85 (3.6 g, 9 mmol) was dissolved in ethyl acetate (350 ml). The flask was degassed and then 10% palladium on carbon (400 mg) was added and the mixture stirred under an atmosphere of hydrogen for 45 mins. The solution was filtered through Celite™ and evaporated. The clear oil obtained was purified by preparative tlc eluting with 5% ethyl acetate in hexanes. The oil obtained was then further purified by column chromatography on silica gel eluting with 5–10% ethyl acetate in hexane to give the product. $^1$H NMR (CDCl$_3$) 7.37–7.34 (4H, m), 7.08–7.00 (2H, m), 6.85–6.81 (1H, m), 3.67 (3H, s), 2.45–2.39 (4H, m), 2.33 (2H, t, J=8.4 Hz), 1.81 (2H, q, J=8.4 Hz), 1.72–1.68 (2H,m) and 1.60–1.43 (3H, m).

Example 87

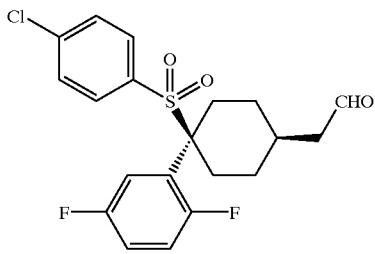

A solution of cis-4-[(4-chlorophenyl)sulfonyl]-4-(2,5-difluorophenyl)cyclohexaneacetonitrile (Example 45) (967.3 g, 2.36 mol) in toluene (15.8 L) and dichloromethane (4.85 L) was cooled to −63° C. and diisobutyl aluminium hydride (1.0M in toluene, 2.48 Kg, 2.89 mol) was added over 60 minutes. Stirring was continued at −60° C. for a further 30 minutes before the solution was transferred into 0.75M citric acid (25 L). The bi-phasic mixture was stirred overnight at 20° C., the layers were separated and the organic layer was washed with 2M hydrochloric acid (15.8 L), 10% sodium bicarbonate (15.8 L) and water (15.8 L). After evaporation of the solvents, the residue was crystallised from EtOAc/heptane to afford cis-4-[(4-chlorophenyl)sulfonyl]-4-(2,5-difluorophenyl)cyclohexaneacetaldehyde (922 g; 95% yield). $^1$H NMR (CD$_2$Cl$_2$) 9.65 (1H, t, J=1.7 Hz), 7.32–7.20 (4H, m), 6.98–6.88 (2H, m) 6.85–6.72 (1H, m), 2.57–2.45 (2H, m), 2.45–2.10 (5H, m) and 1.68–1.35 (4H, m).

Example 88

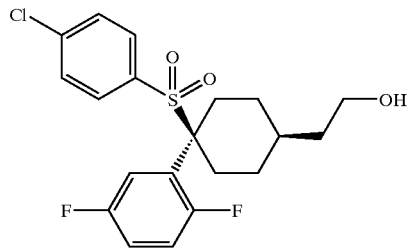

Sodium borohydride (97.9 g, 2.59 mol) was added to a solution of cis-4-[(4-chlorophenyl)sulfonyl]-4-(2,5-difluorophenyl)-cyclohexaneacetaldehyde (922 g, 2.24 mol) (Example 87) in absolute ethanol (6.3 L) and toluene (500 mL). The reaction was stirred at 4° C. for 60 minutes before hydrochloric acid (2M, 2.43 L) was added. The mixture was allowed to warm to 20° C. and stirred until a clear solution was obtained. The latter was transferred into tert-butyl methyl ether (15.8 L) and water (15.8 L), the layers were separated and the organic layer was washed with water (15.8 L). The solution was evaporated to dryness, and 2.4 L toluene was added to the residue. After the product crystallized, n-heptane (480 mL) was added. The slurry was filtered and washed with cold heptane (1 L). The solid was dried under vacuum at 38° C. to provide cis-4-[(4-chlorophenyl)sulfonyl]-4-(2,5-difluorophenyl)cyclohexaneethanol (650 g). Another 144 g was obtained via chromatography of the mother liquors on silica gel, eluting with 30% ethyl acetate in hexanes (combined yield 85%).

$^1$H NMR CDCl$_3$ 7.37–7.30 (4H, m), 7.10–7.00 (2H, m), 6.86–6.79 (1H, m), 3.73–3.68 (2H, m), 2.42–2.36 (4H, m), 1.78–1.69 (5H, m) and 1.53–1.43 (2H, m).

Example 89

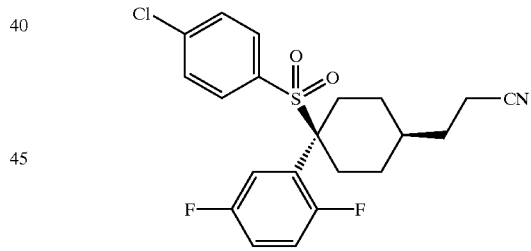

A solution of cis-4-[(4-chlorophenyl)sulfonyl]-4-(2,5-difluorophenyl)cyclohexaneethanol (Example 88) (790 g, 1.9 mol) in dichloromethane (7.9 L) was cooled to −25° C. and triethylamine (344 ml, 2.47 mol) was added followed by methanesulfonyl chloride (154 ml, 1.99 mol) whilst maintaining the temperature below −25° C. The reaction mixture was aged for 90 min. and then quenched into water (7.9 L). The layers of the resulting 2-phase mixture were separated. The organic layer was washed with brine (4 L), the brine layer extracted with dichloromethane (2 L), the combined organic layers dried over sodium sulfate, and then concentrated to dryness. The residue was dissolved in dimethyl sulphoxide (7.9 L), and potassium cyanide (161 g, 2.47 mol) was added. The solution was stirred at ambient temperature for 16 hours, warmed to 30° C. for 3 hours, and then transferred into a mixture of isopropyl acetate (8 L) and water (16 L). Further isopropyl acetate (30 L) and water (30

L) were added. The layers were separated, and the combined organic layers were washed with water (8 L). The organic layer was concentrated to dryness, and the product purified by chromatography on silica gel, eluting with dichloromethane, to give cis-4-[(4-chlorophenyl)sulfonyl]-4-(2,5-difluorophenyl)cyclohexanepropionitrile (697 g, 87%). $^1$H NMR CDCl$_3$ 7.37–7.29 (4H, m), 7.09–7.00 (2H, m), 6.86–6.79 (1H, m), 2.47–2.37 (6H, m), 1.86–1.81 (2H, m), 1.78–1.72 (3H, m) and 1.61–1.52 (2H, m).

Example 90

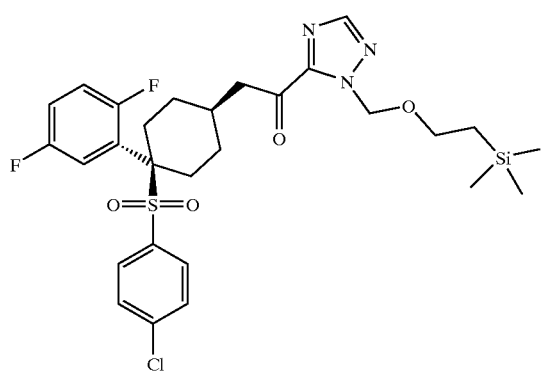

To a cooled (−80° C.) solution of 1-(trimethylsilylethyloxymethyl)-triazole (0.109 g, 0.55 mmol) in tetrahydrofuran (2 ml) was added a solution of n-butyl lithium (2.5M in hexanes, 0.22 ml). The solution was stirred at −80° C. for 15 minutes, warmed to 0° C. for 5 minutes and then recooled to −80° C. To the cooled solution was added a solution of cis-4-[(4-chlorophenyl)sulfonyl]-4-(2,5-difluorophenyl) cyclohexaneacetic acid N,O-dimethylhydroxamate (Example 82) (217 mg, 0.46 mmol) in tetrahydrofuran (3 ml). After stirring the mixture at −80° C. for 15 minutes a saturated solution of aqueous ammonium chloride was added and the product extracted with ethyl acetate. The organic phase was dried (MgSO$_4$), evaporated to dryness and purified by chromatography on silica gel (eluting with 25% ethyl acetate in hexane) to give the desired product as a crystalline solid. MS m/z 610,612 (M+H)

Example 91

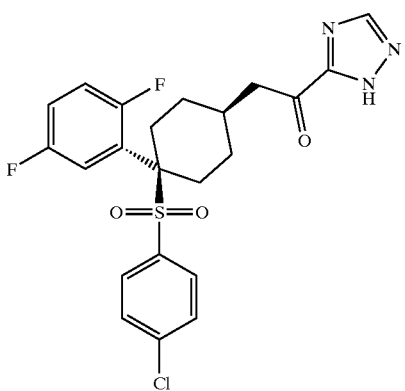

The triazole from Example 90 (0.117 g) was heated in a mixture of ethanol (10 ml) and 6M-HCl (aqueous) (5 ml) and concentrated HCl (2 ml) for 2 hours at 60° C. Water and ethyl acetate were added and the organic phase was dried (MgSO$_4$), evaporated in vacuo and the residue purified by chromatography on silica gel (eluting with 50% ethyl acetate in hexane, 100% ethyl acetate) to give the desired product as a solid which was washed with hexane mp 147–154° C. MS m/z 480,482 (M+H). $^1$H NMR (360 MHz, CD$_4$OD) 1.51–1.60 (2H, m), 1.76 (2H, dd, J=14.3 Hz and 3.1 Hz), 2.37 (1H, m), 2.5 (4H m),3.26 (2H, d, J=7.3 Hz), 6.96 (1H, m), 7.16 (2H, m), 7.40 (2H, dt, J=8.7 Hz and 2.23 Hz), 7.51 (2H, dt, J=8.7 Hz and 2.23 Hz), 8.51 (1H, s).

Example 92

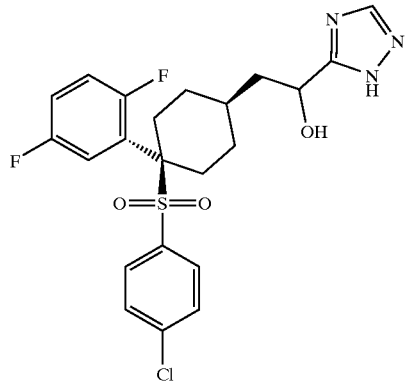

To a solution of the product of Example 91, (50 mg) in methanol (2 ml) was added sodium borohydride (4.5 mg 0.11 mmol). After 30 minutes ethyl acetate and water were added followed by addition of solid citric acid (50 mg). The organic phase was dried (MgSO$_4$), evaporated to dryness and the residue chromatographed on silica gel (eluting with ethyl acetate then 5% methanol in ethyl acetate) to give the desired product as a colourless solid after washing the residue with hexane. MS m/z 482, 484(M+H)). $^1$H NMR (360 MHz, CD$_3$OD) 1.43–1.54 (2H, m), 1.75–1.88 (3H, m), 1.54–2.0 (1H, m), 2.01–2.16 (1H,m), 2.35–2.55(5H,m), 6.93–7.00 (1H, m), 7.09–7.18 (2H, m), 7.37 (2H, d, J=8.6 Hz), 7.48 (2H,d, J=8.6 Hz), 8.1 (1H, v.broad s).

Example 93

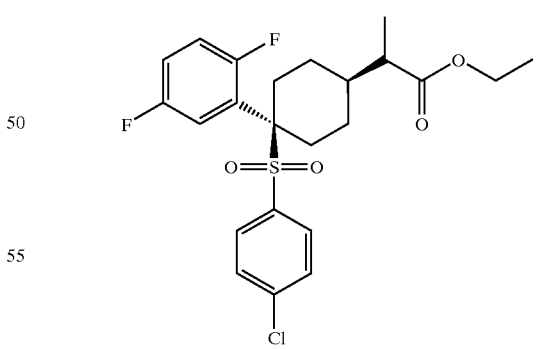

The cis-ester from Example 1 (669 mg, 1.467 mmol) in tetrahydrofuran (14 ml) was cooled to −78° C., treated with sodium bis(trimethylsilyl)amide (2.20 ml, 1 M solution in tetrahydrofuran, 2.20 mmol) and stirred while warming to room temperature over 2 hours. Methyl iodide (457 μl, 7.36 mmol) was then added to the mixture at −20° C. and stirring continued, again warming to room temperature, for 2 hours.

The reaction was quenched with glacial acetic acid (132 μl, 2.20 mmol), diluted with ammonium chloride (50% aq., 80 ml) and extracted with ethyl acetate (3×100 ml). Combined organics were then washed with brine (sat., 200 ml), dried (MgSO$_4$) and evaporated in vacuo to give crude (670 mg). This material was chromatographed on silica, eluting with 8% ethyl acetate in hexanes to give product (272 mg, 40%). $^1$H NMR (400 MHz, CDCl$_3$), 1.16 (3H, d, J=6.9 Hz), 1.28 (3H, t, J=7.1 Hz), 1.45–1.51 (2H, m), 1.71–1.77 (2H, m), 1.89–1.94 (1H, m), 2.28–2.48 (3H, br), 2.54–2.60 (1H, m), 2.70–2.74 (1H, m), 4.09–4.18 (2H, m), 6.77–6.84 (1H, m), 6.99–7.08 (2H, m), 7.26–7.36 (4H, m).

Example 94

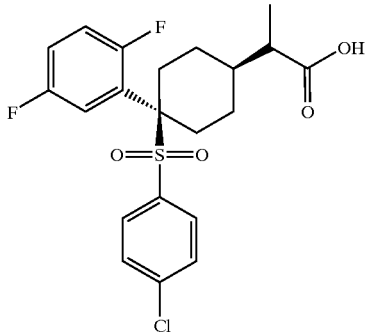

A solution of α-methyl ethyl ester from Example 93 (13 mg, 0.028 mmol) in methanol/water/tetrahydrofuran (3:1:1, 1 ml) was degassed and treated with lithium hydroxide (3.3 mg, 0.138 mmol) and the mixture heated to 90° C. After 1 hour at this temperature, the reaction was cooled to room temperature, acidified with hydrochloric acid (1 N, 2 ml), diluted with water (5 ml) and extracted with ethyl acetate (3×10 ml). Combined organics were washed with brine (sat., 30 ml), dried (MgSO$_4$) and evaporated in vacuo to give crude. This material was purified by preparative t.l.c., eluting with 3% methanol, 1% acetic acid in dichloromethane to give product (7 mg, 57%). $^1$H NMR (360 MHz, CDCl$_3$), 1.22 (3H, d, J=6.9 Hz), 1.48–1.58 (2H, m), 1.74–1.96 (3H, m), 2.30–2.50 (3H, br), 2.53–2.62 (1H, br), 2.71–2.81 (1H, m), 6.78–6.84 (1H, m), 7.00–7.09 (2H, m), 7.30–7.37 (4H, m).

Example 95

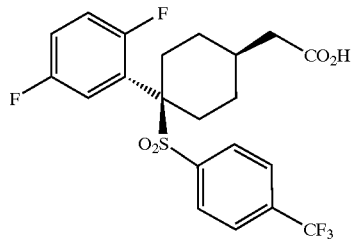

Prepared from the ketone of Preparation 3, following the procedures of Preparation 4 and Examples 1 and 2. $^1$H NMR (360 MHz,CDCl$_3$) 1.52–1.61 (2H, m), 1.76–1.81 (2H, m), 2.20–2.26 (1H, m), 2.39 (2H, d, J=7.6 Hz) 2.40–2.50 (4H, m), 5.37 (1H, br), 5.51 (1H, br), 6.75–6.83 (1H, m), 7.01–7.08 (2H, m), 7.51 (2H, d, J=8.3 Hz) and 7.64 (2H, d, J=8.3 Hz).

Example 96

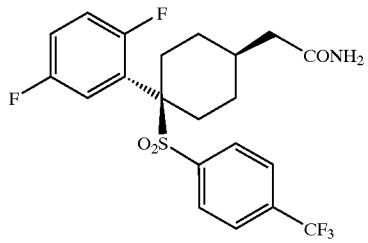

Prepared from the acid of Example 95 by the procedure of Example 40, using ammonia in the second step. MS MH+462(463).

Example 97

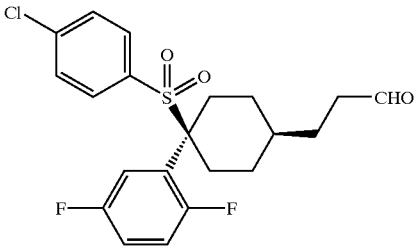

Method (a)

A slurry of methoxymethyltriphenylphosphonium chloride (5.14 g, 15.0 mmol) in toluene (30.0 mL) was cooled to −2° C. and t-BuOK (14.0 mL of a 1M THF solution, 14.0 mmol) was added. The resulting solution was stirred for 30 min and cis-4-[(4-chlorophenyl)sulfonyl]-4-(2,5-difluorophenyl)cyclohexaneacetaldehyde (Example 87) (4.13 g, 10.0 mmol) in toluene (15.0 mL) was added. After the reaction was complete, the mixture was quenched with NH$_4$Cl (10% aq.; 30 mL) and the layers separated. The organics were evaporated to dryness and the resultant solids stirred in DMF (45 mL) with 1N HCl (7.5 mL) at 45° C. After 1 hr, the solution was cooled to 28° C. and water (37.5 mL) was added dropwise. The solids were filtered and washed with DMF:water (33:67, 10 mL) and water (10 mL). Drying overnight in vacuo at 40° C. under a nitrogen stream furnished cis-4-[(4-chlorophenyl)sulfonyl]-4-(2,5-difluorophenyl)-cyclohexanepropanal (4.04 g, 95%). $^1$H NMR (CD$_2$Cl$_2$) 9.67 (1H, t, J=1.5 Hz), 7.32–7.20 (4H, m), 7.03–6.90 (2H, m), 6.82–6.70 (1H, m), 2.39–2.22 (6H, m), 1.72–1.51 (4H, m) and 1.50–1.30 (3H, m).

Method (b)

To a solution of cis-4-[(4-chlorophenyl)sulfonyl]-4-(2,5-difluorophenyl)cyclohexanepropionitrile (Example 89) (627 g, 1.48 mol) in dichloromethane (3.14 L) and toluene (10.19 L) at −60° C. under nitrogen was added 1.5M diisobutyl aluminium hydride (1.14 Kg, 2.0 mol) over 1 hour. The resulting solution was transferred into 0.75M citric acid solution (25 L), and the bi-phasic solution was stirred at room temperature overnight. The layers were separated and the organic phase was washed with 2M hydrochloric acid (17 L), water (20 L), and brine (1 L). Concentration to dryness provided crude cis-4-[(4-chlorophenyl)sulfonyl]-4-(2,5-difluorophenyl)cyclohexanepropanal as a white solid. $^1$H NMR CDCl$_3$—as for Method (a).

Example 98

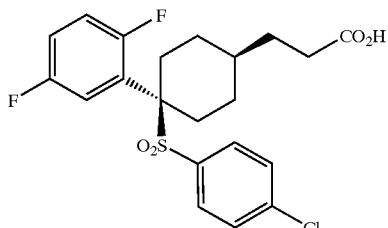

Method (a)

The ester from Example 86 (104 mg, 0.23 mmol) was dissolved in a mixture of ethanol (10 ml) and water (3 ml) and stirred at 20° C. The flask was degassed and then lithium hydroxide (27 mg, 1.15 mmol) was added. The mixture was stirred for 3 hrs. at room temperature. 1N Hydrochloric acid was then added and the mixture was washed with ethyl acetate (2×50 ml). The organic phase was washed with brine (50 ml), dried (MgSO$_4$) and evaporated. The oil obtained was then further purified by preparative tlc eluting with ethyl acetate to give the acid. $^1$H NMR (CDCl$_3$) 7.37–7.30 (4H, m), 7.09–6.99 (2H, m), 6.85–6.79 (1H, m), 2.42–2.36 (6H, m), 1.85–1.79 (2H, m), 1.73–1.69 (2H,m), 1.63–1.58 (1H, m) and 1.53–1.45 (2H, m).

Method (b)

To a solution of crude cis-4-[(4-chlorophenyl)sulfonyl]-4-(2,5-difluorophenyl)cyclohexanepropanal (Example 97, method (b)) (650 g, 1.52 mol) in CH$_2$Cl$_2$ (6 L) and H$_2$O (6 L) was added sulfamic acid (215.5 g, 2.21 mol) followed by slow addition of sodium chlorite (180 g in 3.13 L H$_2$O, 2.0 mol) over 30 min. maintaining the internal temperature below 30° C. The phases were separated and the organic layer was washed with an aqueous Na$_2$S$_2$O$_5$ solution (157 g in 20 L H$_2$O), water (20 L) and then dried (Na$_2$SO$_4$). The solution was concentrated in vacuo and the residue was recrystallised from IPAc/heptane to afford cis-4-[(4-chlorophenyl)sulfonyl]-4-(2,5-difluorophenyl)cyclohexanepropanoic acid (482 g, 74%). $^1$H NMR as for product of method (a).

A sample of this product (100 g, 0.226 mol) was dissolved in isopropanol (2000 mL) at 45° C. and treated with 2M aqueous sodium hydroxide solution (112 mL, 0.224 mol). The resulting solution was distilled at atmospheric pressure to remove 1000 mL of distillate, then fresh isopropanol (1000 mL) was added and the distillation process repeated. More isopropanol (1000 mL) was added and the distillation process repeated once more. Crystallisation of the sodium salt began during the distillation process. The reaction mixture was allowed to cool to ambient temperature, aged for 1 hour and then filtered. The filter cake was washed with isopropanol (200 mL) and then dried overnight at 40° C. in vacuo to furnish the sodium salt of cis-4-[(4-chlorophenyl)sulfonyl]-4-(2,5-difluorophenyl)cyclohexanepropanoic acid (95 g) in 91% yield.

Example 99

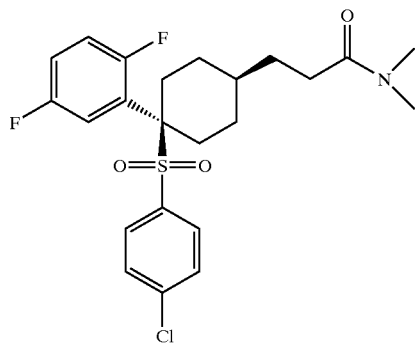

The acid from Example 98 (52 mg, 0.118 mmol) in dichloromethane (2 ml) was treated with oxalyl chloride (88 µl, 2 M solution in dichloromethane, 0.176 mmol). A drop of N,N-dimethylformamide was added and the solution allowed to stir for 2 hours. After this time, solvent was removed in vacuo and the residue redissolved in dichloromethane (1 ml). This solution was dripped into methanolic ammonia (2 M, 2 ml). The reaction was evaporated in vacuo and the residue chromatographed on silica, eluting with 80% ethyl acetate in hexanes. The resulting material was purified further by preparative t.l.c., eluting with 100% ethyl acetate followed by recrystallisation from hot hexane to give product (7.4 mg, 14%). $^1$H NMR (360 MHz, CDCl$_3$), 1.45–1.53 (2H, m), 1.57–1.65 (1H, br), 1.70–1.75 (2H, m), 1.78–1.84 (2H, m), 2.32 (2H, t, J=15.3 Hz), 2.38–2.44 (4H, br), 2.95 (3H, s), 3.02 (3H, s), 6.79–6.86 (1H, m), 7.00–7.09 (2H, m), 7.31–7.37 (4H, m); ms. (ES$^+$), 470 (M$^+$1), 294 (M$^+$175).

Example 100

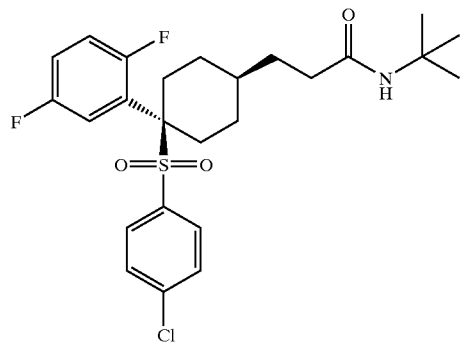

The acid from Example 98 (52 mg, 0.118 mmol) in dichloromethane (2 ml) was treated with 1-(3-dimethylaminopropyl)-3-ethylcarbodiimide hydrochloride (45 mg, 0.235 mmol), triethylamine (32.7 µl, 0.235 mmol) and tert-butylamine (24.6 µl, 0.235 mmol). After 2 hours stirring at room temperature, reaction was washed with hydrochloric acid (1 N, 10 ml), organics dried (MgSO$_4$) and evaporated in vacuo to give crude (55 mg). This material was chromatographed on silica, eluting with 20–30% ethyl acetate in hexanes to give product (25 mg, 43%). $^1$H NMR (400 MHz, CDCl$_3$), 1.35 (9H, s), 1.45–1.62 (3H, m), 1.67–1.74 (2H, m), 1.76–1.80 (2H, m), 2.08–2.12 (2H, m), 2.38–2.42 (4H, br), 5.72–5.78 (1H, br), 6.76–6.88 (1H, m), 7.00–7.10 (2H, m), 7.31–7.37 (4H, m).

Example 101

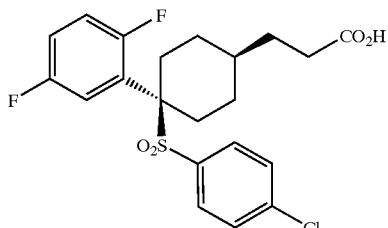

Prepared from the ketone of Preparation 3 following the procedures of Preparations 5–8 and Examples 54, 85, 86 and 98, method (a).

$^1$H NMR (360 MHz, CDCl$_3$) δ 10.1 (1H, m), 7.64 (2H, d, J=8.3 Hz), 7.53 (2H, d, J=8.3 Hz), 7.09–7.00 (2H, m), 6.83–6.76 (1H, m), 2.50–2.37 (6H, m), 1.85–1.81 (2H, q, J=7.4 Hz), 1.75–1.70 (2H, m), 1.63–1.59) (1H, m), 1.55–1.45 (2H, m). MS(EI$^+$) 477 (MH$^+$).

What is claimed is:

1. A compound of formula I:

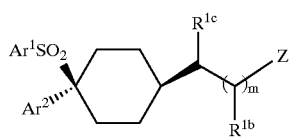

wherein:
m is 0 or 1;
Z represents CO$_2$R$^{2a}$;
R$^{1b}$ represents H, C$_{1-4}$alkyl or OH;
R$^{1c}$ represents H or C1-4alkyl;
with the proviso that when m is 1, R$^{1b}$ and R$^{1c}$ do not both represent C$_{1-4}$alkyl;
Ar$^1$ represents C$_{6-10}$aryl, which bears 0–3 substituents independently selected from halogen, NO$_2$, CF$_3$, OH, OCF$_3$, C$_{1-4}$alkoxy or C$_{1-4}$alkyl which optionally bears a substituent selected from halogen, NO$_2$, CF$_3$, OH and C$_{1-4}$alkoxy;
Ar$^2$ represents C$_{6-10}$aryl, which bears 0–3 substituents independently selected from halogen, NO$_2$, CF$_3$, OH, OCF$_3$, C$_{1-4}$alkoxy or C$_{1-4}$alkyl which optionally bears a substituent selected from halogen, NO$_2$, CF$_3$, OH and C$_{1-4}$alkoxy;
R$^{2a}$ represents H;
or a pharmaceutically acceptable salt thereof.

2. A compound according to claim 1 wherein Ar$^1$ is substituted in the 4-position with halogen, methyl or trifluoromethyl, or substituted in the 3- and 4-positions by halogen.

3. A compound according to claim 1 wherein Ar$^2$ is substituted in the 2- and 5-positions by halogen.

4. A compound according to claim 1 wherein m is 1, Ar$^1$ represents 4-chlorophenyl, Ar$^2$ represents 2,5-difluorophenyl, and R$^{1b}$ and R$^{1c}$ both represent H.

5. A compound according to claim 1 wherein m is 1, Ar$^1$ represents 4-trifluoromethylphenyl, Ar$^2$ represents 2,5-difluorophenyl, and R$^{1b}$ and R$^{1c}$ both represent H.

6. A pharmaceutical composition comprising a compound of formula I as defined in claim 1, or a pharmaceutically acceptable salt thereof, and a pharmaceutically acceptable carrier.

7. A method of treatment of a subject suffering from Alzheimer's Disease which comprises administering to that subject an effective amount of a compound of formula I as defined in claim 1 or a pharmaceutically acceptable salt thereof.

8. A compound which is:

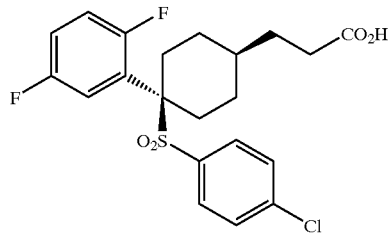

or a pharmaceutically acceptable salt thereof.

9. A compound which is:

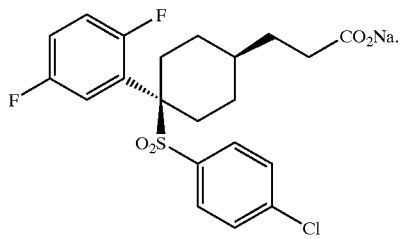

10. A pharmaceutical composition comprising a compound which is:

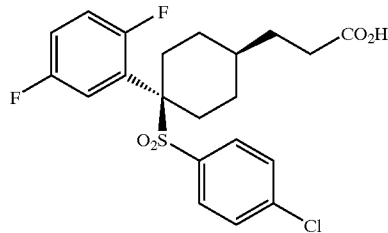

or a pharmaceutically acceptable salt thereof, and a pharmaceutically acceptable carrier.

11. A method for the treatment of a patient suffering from Alzheimer's Disease which comprises administering to the patient an effective amount of the compound:

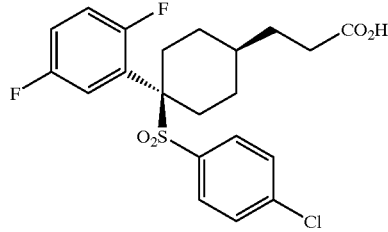

or a pharmaceutically acceptable salt thereof.

* * * * *